(12) United States Patent
Wu et al.

(10) Patent No.: US 10,898,486 B2
(45) Date of Patent: Jan. 26, 2021

(54) CRYSTAL FORM OF OREXIN RECEPTOR ANTAGONIST COMPOUND, AND PREPARATION METHOD AND APPLICATION THEREOF

(71) Applicants: Shanghai Haiyan Pharmaceutical Technology Co., Ltd., Shanghai (CN); Yangtze River Pharmaceutical Group Co., Ltd., Taizhou (CN)

(72) Inventors: Songliang Wu, Shanghai (CN); Zhi Luo, Shanghai (CN); Yuan Chen, Shanghai (CN); Yuhe Wang, Shanghai (CN); Dakun Qin, Shanghai (CN); Xiaolin Li, Shanghai (CN); Zheng Wang, Shanghai (CN); Weidong Li, Shanghai (CN); Haiying He, Shanghai (CN)

(73) Assignees: SHANGHAI HAIYAN PHARMACEUTICAL TECHNOLOGY CO., LTD., Shanghai (CN); YANGTZE RIVER PHARMACEUTICAL GROUP CO., LTD., Jiangsu (CN)

(*) Notice: Subject to any disclaimer, the term of this patent is extended or adjusted under 35 U.S.C. 154(b) by 0 days.

(21) Appl. No.: 16/864,153

(22) Filed: Apr. 30, 2020

(65) Prior Publication Data

US 2020/0261453 A1 Aug. 20, 2020

Related U.S. Application Data

(62) Division of application No. 15/752,290, filed as application No. PCT/CN2016/094558 on Aug. 11, 2016, now Pat. No. 10,668,066.

(30) Foreign Application Priority Data

Aug. 14, 2015 (CN) .......................... 2015 1 0501331

(51) Int. Cl.
| | | |
|---|---|---|
| *C07D 451/02* | (2006.01) | |
| *A61K 31/506* | (2006.01) | |
| *A61K 31/46* | (2006.01) | |
| *A61P 25/34* | (2006.01) | |
| *A61P 25/20* | (2006.01) | |
| *A61P 25/22* | (2006.01) | |
| *A61P 11/08* | (2006.01) | |

(52) U.S. Cl.
CPC ............ *A61K 31/506* (2013.01); *A61K 31/46* (2013.01); *A61P 11/08* (2018.01); *A61P 25/20* (2018.01); *A61P 25/22* (2018.01); *A61P 25/34* (2018.01); *C07D 451/02* (2013.01)

(58) Field of Classification Search
CPC .............................. C07D 451/02; A61K 31/506
USPC ......................................... 544/333; 514/256
See application file for complete search history.

(56) References Cited

U.S. PATENT DOCUMENTS 6,627,646 B2 9/2003 Bakale et al.
2017/0233385 A1 8/2017 He et al.

FOREIGN PATENT DOCUMENTS

| WO | 2008147518 A1 | 12/2008 |
| WO | 2009104155 A1 | 8/2009 |
| WO | 2009153178 A2 | 12/2009 |
| WO | 2014159591 A1 | 10/2014 |
| WO | 2014165070 A1 | 10/2014 |
| WO | 2015131773 A1 | 9/2015 |

OTHER PUBLICATIONS

"Concise Encyclopedia Chemistry", Walter de Gruyter Berlin, New York, pp. 872-873 (1994).
Abreu et al., "Role of medial hypothalamic orexin system in panic, phobia and hypertension", Brain Research, pp. 1-8 (2018), at https://doi.org/10.1016/j.brainres.2018.09.010.
Barson, "Orexin/hypocretin and dysregulated eating: Promotion of foraging behavior", Brain Research, pp. 1-9 (2018), at https://doi.org/10.1016/j.brainres.2018.08.016.
Bernstein, "Polymorphism in Molecular Crystals", pp. 115-118, "Polymorphism of Dyes and Pigments", p. 272, X-Ray Crystallography, Clarendon Press, Oxford (2002).
Braga et al., "Making crystals from crystals: a green route to crystal engineering and polymorphism", Chem. Commun., pp. 3635-3645 (2005).
CMU Seed Fund Project on Detection and Control of Pharmaceutical Polymorphism, pp. 1-3 printout (2008), at http://andrew.cmu.edu/user/suter/polymorph.html.
Davidovich et al., "Detection of Polymorphism by Powder X-Ray Diffraction: Interference by Preferred Orientation", American Pharmaceutical Review, vol. 2, No. 1, pp. 10, 12, 14, 16, 100 (2004).
Dean, Analytical Chemistry Handbook, 10.24-10.26 (1995).
Doelker, "Crystalline Modifications and Polymorphous Changes During Drug Manufacture", Ann. Pharm Fr., vol. 60, pp. 161-176 (2002).
Doelker, "Physicochemical Behaviors of Active Substances Their Consequences for the Feasibility and the Stability of Pharmaceutical Forms", S.T.P. Pratiques, vol. 9, No. 5, pp. 399-409 (1999).
Grant, "Theory and Origin of Polymorphism", pp. 1-2, and Guillory, "Generation of Polymorphs, Hydrates, Solvates, and Amorphous Solids", pp. 183-226, in Polymorphism in Pharmaceutical Solids, ed. Brittain, Marcel Dekker, New York (1999).
Int'l Search Report dated Nov. 10, 2016 in Int'l Application No. PCT/CN2016/094558.
Ivanisevic et al., "Uses of X-Ray Powder Diffraction in the Pharmaceutical Industry", Pharmaceutical Sciences Encyclopedia: Drug Discovery, Development, and Manufacturing, pp. 1-42 (2010).

(Continued)

*Primary Examiner* — Patricia L Morris
(74) *Attorney, Agent, or Firm* — Panitch Schwarze Belisario & Nadel LLP; Lars H. Genieser

(57) ABSTRACT

Disclosed is a preparation method of an orexin receptor antagonist compound 5-3. Crystalline forms I-IV of an orexin receptor antagonist compound 5-3 are provided. Also provided are processes of preparing crystalline forms of the orexin receptor antagonist compound 5-3, as well as methods of using the crystalline forms I-IV for treating an orexin-related disease.

6 Claims, 2 Drawing Sheets

(56) References Cited

OTHER PUBLICATIONS

Jain et al., "Polymorphism in Pharmacy", Indian Drugs, vol. 23, No. 6, pp. 315-329 (1986).
Johnson et al., "Activation of the Orexin I Receptor is a Critical Component of CO2-Mediated Anxiety and Hypertension but not Bradycardia", Neuropsychopharmacology, vol. 37, pp. 1911-1922 (2012).
Muzaffar et al., "Polymorphism and Drug Availability", Journal of Pharmacy (Lahore), vol. 1, No. 1, pp. 59-66 (1979).
Office Action dated Mar. 27, 2019 in U.S. Appl. No. 15/752,290.
Office Action dated Oct. 10, 2018 in U.S. Appl. No. 15/752,290.
Office Action dated Sep. 27, 2019 in U.S. Appl. No. 15/752,290.
Otsuka et al., "Effect of Polymorphic Forms of Bulk Powders on Pharmaceutical Properties of Carbamazepine Granules", Chem. Pharm. Bull., vol. 47, No. 6, pp. 852-856 (1999).
Perna et al., "Novel investigational therapeutics for panic disorder", Expert Opinion on Investigational Drugs, vol. 24, No. 4, pp. 491-505 (2015).
Restriction Requirement dated Jul. 5, 2018 in U.S. Appl. No. 15/752,290.
Rodriguez-Spong et al., "General principles of pharmaceutical solid polymorphism: a supramolecular perspective", Advanced Drug Delivery Reviews, vol. 56, pp. 241-274 (2004).
Seddon, "Pseudopolymorph: A Polemic", Crystal Growth & Design, vol. 4, No. 6, p. 1087 (2004) (2 printed pages).
Shariq et al., "Evaluating the role of orexins in the pathophysiology and treatment of depression: A comprehensive review", Progress in Neuropsychopharmacology & Biological Psychiatry, vol. 92, pp. 1-7 (2019).
Sheng et al., "The Subthalamic Neurons are Activated by Both Orexin-A and Orexin-B", Neuroscience, vol. 369, pp. 97-108 (2018).
Sieminski et al., "Orexins, Sleep and Blood Pressure", Current Hypertension Reports, vol. 20, No. 79, pp. 1-8 (2018), at https://doi.org/10.1007/s11906-018-0879-6.
Singhal et al., "Drug polymorphism and dosage form design: a practical perspective," Advanced Drug Delivery Reviews, vol. 56, pp. 335-347 (2004).
Strother et al., "Targeted Orexin and Hypothalamic Neuropeptides for Migraine", Neurotherapeutics, vol. 15, pp. 377-390 (2018).
Taday et al., "Using Terahertz Pulse Spectroscopy to Study the Crystalline Structure of a Drug: A Case Study of the Polymorphs of Ranitade Hydrochloride", J. of Pharm. Sci., vol. 92, No. 4, pp. 831-838 (2003).
Ulrich, "Crystallization", Kirk-Othmer Encyclopedia of Chemical Technology, vol. 8, pp. 95-147 (2002).
Vippagunta et al., "Crystalline solids", Advanced Drug Delivery Reviews, vol. 48, pp. 3-26 (2001).
Zarrabian et al., "The potential role of the orexin reward system in future treatements for opioid drug use", Brain Research, pp. 1-10 (2018), at https://doi.org/10.1016/j.brainres.2018.11.023.

CRYSTAL FORM OF OREXIN RECEPTOR ANTAGONIST COMPOUND, AND PREPARATION METHOD AND APPLICATION THEREOF

CROSS-REFERENCE TO RELATED APPLICATION

This application is a Divisional of U.S. patent application Ser. No. 15/752,290, filed Feb. 13, 2018, which is a Section 371 of International Application No. PCT/CN2016/094558, filed Aug. 11, 2016, which was published in the Chinese language on Feb. 23, 2017, under International Publication No. WO 2017/028732 A1, which claims priority under 35 U.S.C. § 119(b) to Chinese Application No. 201510501331.8, filed Aug. 14, 2015, the disclosures of which are incorporated herein by reference in their entirety.

TECHNICAL FIELD

The present invention relates to crystalline form I, crystalline form II, crystalline form III and crystalline form IV of the compound 5-3 as orexin receptor antagonist and its preparation method, and its application in the manufacture of medicaments for the treatment of orexin-related diseases.

BACKGROUND

Orexin (or orexins) includes two neuropeptides produced by the hypothalamus: the orexin A (OX-A) (a peptide with 33 amino acids) and the orexin B (OX-B) (a peptide with 28 amino acids) (Sakurai T., et al., Cell, 1998, 92, 573-585). It is found that orexin can stimulate food consumption in rats, that is to say, in the center feedback mechanism of regulation of feeding behavior, the peptide has a physiological role as a medium (Sakurai T. et al., Cell, 1998, 92, 573-585). Orexin can regulate sleep and insomnia status, thereby potentially providing a new method for treatment of sleep in patients with insomnia or paroxysmal (Chemelli R. M. et al., Cell, 1999, 98, 437-451). Orexin also play a role in awakening, motivation, learning and memory (Harris, et al., Trends Neurosci., 2006, 29 (10), 571-577). Two orexin receptors have been cloned and characterized in mammals, which belong to the G protein-coupled receptor superfamily (Sakurai T. et al., Cell, 1998, 92, 573-585): the orexin-1 receptor (OX or OX1R) is selective for OX-A, and orexin-2 receptor (OX2 or OX2R) is capable of binding OX-A and OX-B. It is believed that the physiological role of orexin is assumed to be expressed with either or both of OX1 receptor and OX2 (two subtypes of orexin receptor).

Orexin receptors can be found in brain of warm-blooded animals, and are involved in many diseases, e.g., depression; anxiety; addiction; obsessive compulsory disorder; affective neurosis; depressive neurosis; anxiety neurosis; dysthymic disorder; behavioral disorders; mood disorders; sexual dysfunction; psychosexual dysfunction; gender disorder; schizophrenia: manic depression; delirium; dementia; severe mental retardation and movement disorders, such as Huntington's disease and Tourette syndrome; eating disorders such as anorexia, bulimia, cachexia, and obesity; addictive feeding behavior; binge eating crash feeding behavior; cardiovascular disease; diabetes; appetite or taste disorders; emesis, vomiting, nausea; asthma: cancer, Parkinson's disease; Cushing's syndrome/disease; basophil adenoma; prolactinoma; hyperprolactinemia; pituitary tumor or adenoma; hypothalamic disease; inflammatory bowel disease; gastric dysfunction; gastric ulcer; obesity genital degradation; pituitary disorders; pituitary gland disorders; pituitary hypogonadism; pituitary hyperactivity; hypothalamic hypogonadism; Kallmann's comprehensive disease (anosmia, hyposmia); functional or psychogenic amenorrhea; hypopituitarism; hypothalamic hypothyroidism; hypothalamus-adrenal dysfunction; sudden hyperprolactinemia; hypothalamic disease growth hormone deficiency; sudden lack of growth; dwarfism; gigantism; acromegaly; disturbed biological and circadian rhythms; sleep disorders associated with diseases such as neurological disorders, neuropathic pain and restless leg syndrome; heart and lung diseases, acute and congestive heart failure; hypotension; hypertension; urinary retention; osteoporosis; angina; acute myocardial infarction; ischemic or hemorrhagic stroke; subarachnoid hemorrhage; ulcers; allergic reaction; benign prostatic hypertrophy; chronic renal failure; kidney disease; impaired glucose tolerance; migraine; hyperalgesia; pain; enhanced or exaggerated sensitivity to pain such as hyperalgesia, causalgia and allodynia; acute pain; burning pain; atypical facial pain; neuropathic pain; back pain; complex regional pain syndrome I and II; arthritic pain; sports injury pain; and infections (such as HIV) related pain, post-chemotherapy pain; post-stroke pain; post-operative pain; neuralgia; vomiting, nausea, vomiting; visceral pain related disorders, such as irritable bowel syndrome and angina; migraine; urinary bladder incontinence, for example, urge incontinence; tolerance to narcotics or anesthetics; sleep disorders; sleep apnea; narcolepsy; insomnia; parasomnia; jet lag syndrome; and neurodegenerative disorders, including disease classification entities such as disinhibition-dementia-Parkinson's-muscular atrophy syndrome; epilepsy: seizure disorders and other general orexin system dysfunction related diseases.

Preparation of intermediate of ester compounds through hydrogenation reduction of alkene has been reported in the previous literatures. WO2009153178, WO2012036997, WO2012058127 have reported hydrogenation reduction using palladium carbon and palladium hydroxide. However, none of these references studied the effect of hydrogenation conditions on cis- and trans-products.

SUMMARY OF THE INVENTION

The object of the present invention is to provide a preparation method of compound 5-3, which includes the following steps:

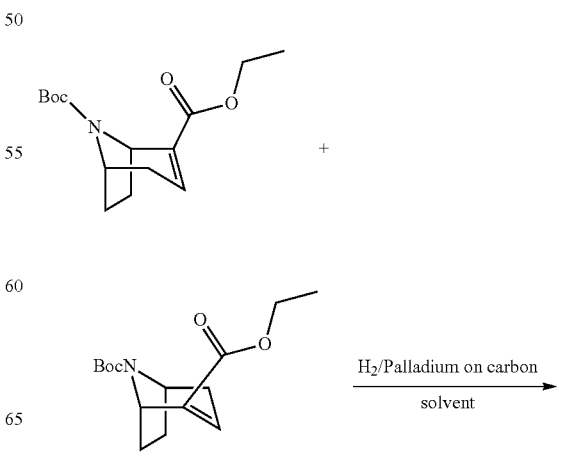

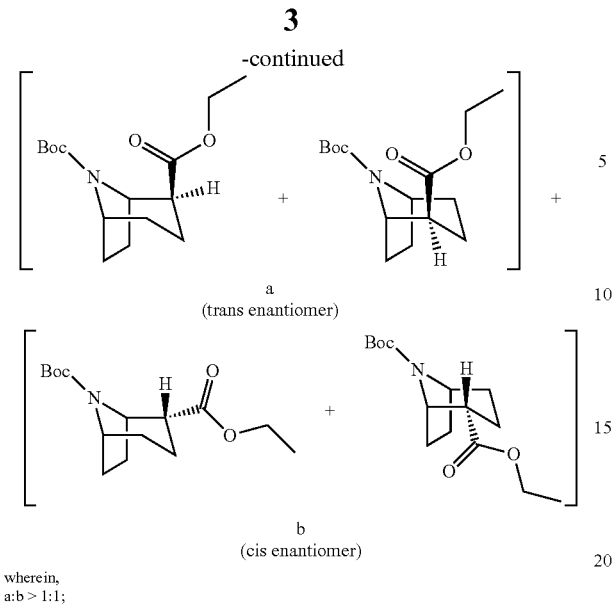

a
(trans enantiomer)

b
(cis enantiomer)

wherein,
a:b > 1:1;

the reaction pressure is normal pressure to 10 Mpa;

optionally, the reaction temperature is 0° C. to room temperature;

the reaction solvent is selected from the polar organic solvent.

In one embodiment of the present invention, a:b>3:1.

In one embodiment of the present invention, the reaction pressure is 1 Mpa to 5 Mpa.

In one embodiment of the present invention, optionally, the reaction temperature is 5 to 10° C.

In one embodiment of the present invention, the above mentioned polar organic solvent is selected from ethyl acetate, tetrahydrofuran, methanol, ethanol, isopropanol, or dioxane.

The object of the present invention is to provide a preparation method of compound 5-3, which includes the following steps:

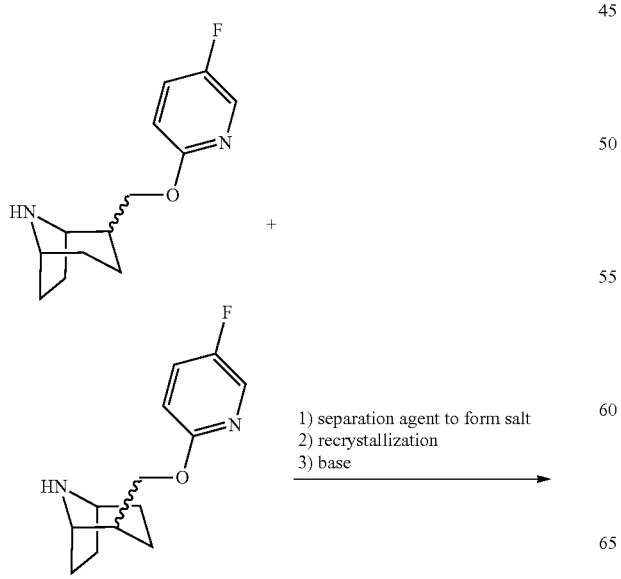

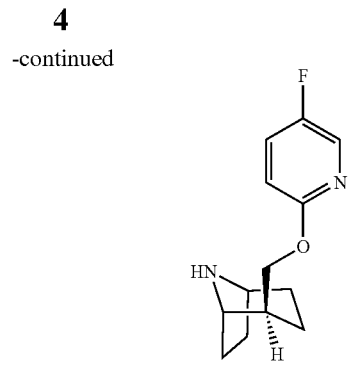

wherein, the separation agent is selected from D-tartaric acid;

the reaction solvent is selected from ethyl acetate, isopropyl acetate, ethanol, methanol, tetrahydrofuran, dichloromethane or water;

the recrystallization solvent is selected from water, or ethanol;

the base is selected from sodium carbonate, potassium carbonate, sodium hydroxide, or potassium hydroxide.

In one embodiment of the present invention, the preparation method of compound 5-3 includes the following steps:

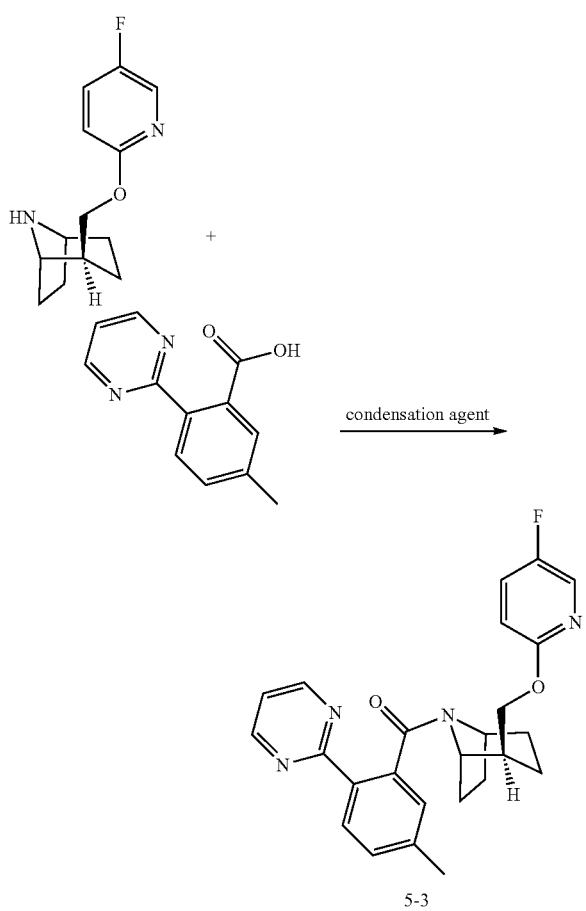

wherein the condensation agent is selected from $T_3P$, CDI, EDCI, HOBt or HATU.

The object of the present invention is to provide crystal form I of compound 5-3, whose structure is shown in FIG. 1.

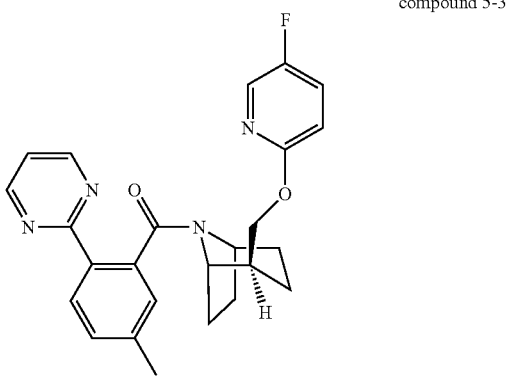

compound 5-3

In one embodiment of the present invention, the XRPD pattern analysis of crystal form I of compound 5-3 is as follows.

| diffraction angle 2θ | relative intensity (%) |
|---|---|
| 8.611 | 100.0 |
| 10.330 | 70.6 |
| 12.284 | 13.4 |
| 13.703 | 23.9 |
| 14.057 | 5.6 |
| 14.351 | 4.8 |
| 14.848 | 9.2 |
| 15.576 | 7.5 |
| 16.602 | 31.6 |
| 17.250 | 71.3 |
| 17.902 | 90.7 |
| 18.277 | 42.4 |
| 19.149 | 6.5 |
| 20.625 | 21.7 |
| 21.550 | 42.7 |
| 22.124 | 2.3 |
| 23.307 | 33.4 |
| 23.953 | 2.6 |
| 24.370 | 32.3 |
| 26.501 | 29.4 |
| 26.915 | 8.7 |
| 27.663 | 11.0 |
| 27.939 | 15.5 |
| 29.499 | 2.6 |
| 30.604 | 2.2 |
| 31.727 | 13.3 |
| 32.969 | 2.6 |
| 33.378 | 2.8 |
| 33.777 | 3.0 |
| 34.825 | 1.6 |
| 36.399 | 5.3 |
| 37.366 | 4.3 |
| 39.357 | 3.3 |

The present invention also provides a method for preparing crystal form I, which comprises that adding compound 5-3 into a polar organic solvent, heating to a temperature from 40° C. to reflux temperature for dissolution, and then slowly adding a weak polar or non-polar organic solvent dropwise, and after the addition is completed, cooling to a temperature of 0-20° C. in 1-10 hours, thereby forming the crystal.

In one embodiment of the present invention, the above polar organic solvent is selected from $C_{1-6}$ alkyl alcohol, $C_{2-6}$ ester, acetonitrile and/or dichloromethane, or a mixture thereof.

In one embodiment of the present invention, the above $C_{1-6}$ alkyl alcohol is selected from methanol, ethanol, isopropanol, and/or n-butanol.

In one embodiment of the present invention, the above $C_{2-6}$ ester is selected from ethyl formate, ethyl acetate, isopropyl acetate, isobutyl acetate, and/or n-butyl acetate.

In one embodiment of the invention, the above weak polar or non-polar organic solvent is selected from $C_{5-10}$ alkane or cycloalkane, $C_{4-10}$ ether or cyclic ether, petroleum ether, and/or benzene optionally substituted by 1 to 3 methyl or ethyl or halogen atoms.

In some embodiments of the present invention, the above $C_{5-10}$ alkane or cycloalkane is selected from pentane, n-hexane, cyclohexane, n-heptane and/or isooctane.

In one embodiment of the invention, the above $C_{4-10}$ ether or cyclic ether is selected from ethyl ether, methyl tert-butyl ether, n-propyl ether, n-butyl ether, ethylene glycol dimethyl ether, tetrahydrofuran, dimethyl tetrahydrofuran and/or dioxane.

In one embodiment of the present invention, the above benzene optionally substituted by 1 to 3 of methyl or ethyl or halogen atoms is selected from methylbenzene, xylene, or chlorobenzene.

In one embodiment of the present invention, the amount (weight/volume) ratio of compound 5-3 to the polar organic solvent is 1:1-10.

In one embodiment of the present invention, the amount (weight/volume) ratio of compound 5-3 to the polar organic solvent is specifically 1:2-5.

In one embodiment of the present invention, the amount (weight/volume) ratio of compound 5-3 to the weak polar or non-polar organic solvent is 1:1-15.

In one embodiment of the present invention, the amount (weight/volume) ratio of compound 5-3 to the weak polar or non-polar organic solvent is specifically 1: 2-7.

The present invention also provides crystal form II of compound 5-3, whose structure is shown in FIG. 2.

In one embodiment of the present invention, the XRPD pattern analysis of crystal form II is as follows.

| diffraction angle 2θ | relative intensity (%) |
|---|---|
| 10.428 | 60.0 |
| 11.968 | 100.0 |
| 13.542 | 17.8 |
| 14.238 | 3.4 |
| 14.767 | 12.1 |
| 15.851 | 73.9 |
| 16.818 | 72.0 |
| 18.003 | 9.2 |
| 19.087 | 2.1 |
| 19.755 | 47.6 |
| 20.900 | 25.7 |
| 22.652 | 2.9 |
| 23.858 | 49.2 |
| 24.844 | 23.2 |
| 25.533 | 8.2 |
| 26.083 | 11.0 |
| 27.133 | 3.1 |
| 27.506 | 17.7 |
| 28.316 | 3.0 |
| 29.557 | 2.2 |
| 30.740 | 4.2 |
| 31.846 | 5.1 |
| 32.550 | 2.0 |
| 33.775 | 3.1 |
| 34.682 | 2.2 |
| 36.422 | 3.4 |
| 36.953 | 3.4 |
| 38.569 | 3.0 |

The present invention also provides a method for preparing crystal form II, which comprises that adding crystal form I or crystal form III or crystal form IV of compound 5-3, or a mixed crystal form or any other form composed of the three crystal forms in any ratio into an organic solvent or a mixed solvent of organic solvent and water, and stirring for 5-120 hours at 20-40° C.

In one embodiment of the present invention, the above organic solvent is selected from $C_{1-6}$ alkyl alcohol, $C_{5-10}$ alkane or cycloalkane, $C_{4-10}$ ether or cyclic ether, $C_{3-7}$ ketone, $C_{2-6}$ ester, acetonitrile and/or benzene optionally substituted by 1-3 methyl or ethyl or halogen atoms.

In one embodiment of the present invention, the $C_{1-6}$ alkyl alcohol is selected from methanol, ethanol, isopropanol, and/or n-butanol.

In one embodiment of the present invention, the $C_{5-10}$ alkane or cycloalkane is selected from pentane, n-hexane, n-heptane and/or cyclohexane.

In one embodiment of the present invention, the above $C_{4-10}$ ether or cyclic ether is selected from methyl tert-butyl ether, tetrahydrofuran, dimethyl tetrahydrofuran and/or 1,4-dioxane.

In one embodiment of the present invention, the $C_{3-7}$ ketone is selected from acetone, methyl isobutyl ketone, and/or methyl ethyl ketone.

In one embodiment of the present invention, the $C_{2-6}$ ester is selected from ethyl acetate, and/or isopropyl acetate.

In one embodiment of the present invention, the benzene optionally substituted by 1-3 of methyl or ethyl or halogen atoms is selected from methylbenzene, xylene, or chlorobenzene.

In one embodiment of the present invention, the mixed solvent of organic solvent and water is selected from methanol/water, ethanol/water, isopropanol/water, acetonitrile/water, acetone/water, tetrahydrofuran/water or 1,4-dioxane/water.

In one embodiment of the present invention, the volume ratio of organic solvent to water is 0.1-20:1.

In some embodiments of the present invention, the organic solvent is selected from isopropanol, acetonitrile, methyl isobutyl ketone, ethyl acetate, isopropyl acetate, dimethyl tetrahydrofuran, toluene, and/or methanol.

In one embodiment of the present invention, the volume ratio of organic solvent to water is specifically 0.5-5:1.

The present invention also provides crystal form III of compound 5-3, whose structure is shown in FIG. 3.

In one embodiment of the present invention, the XRPD pattern analysis of crystal form III is as follows.

| diffraction angle 2θ | relative intensity (%) |
|---|---|
| 8.539 | 57.2 |
| 10.296 | 65.1 |
| 12.283 | 8.3 |
| 14.023 | 6.0 |
| 14.319 | 4.0 |
| 15.879 | 1.6 |
| 17.230 | 100.0 |
| 17.804 | 11.5 |
| 18.005 | 22.4 |
| 19.269 | 1.3 |
| 20.591 | 18.6 |
| 21.514 | 18.5 |
| 23.092 | 2.6 |
| 23.322 | 0.9 |
| 24.319 | 28.5 |
| 26.426 | 7.1 |
| 30.568 | 1.0 |
| 31.686 | 4.6 |
| 33.739 | 0.9 |
| 34.768 | 0.9 |
| 36.366 | 5.1 |
| 37.326 | 0.5 |
| 39.285 | 1.3 |

The present invention also provides a method for preparing crystal form III, which comprises that adding crystal form I of compound 5-3 or any other form of compound 5-3 except crystal form II into a polar organic solvent, dissolving at room temperature or heating to a temperature of 40° C. to reflux temperature for dissolution, and then slowly adding a weak polar or non-polar organic solvent dropwise, and after the addition is completed, forming the crystal at room temperature or by cooling to 20-30° C. in 1-120 hours.

In one embodiment of the present invention, the above organic solvent is selected from $C_{1-6}$ alkyl alcohol, $C_{5-10}$ alkane or cycloalkane, $C_{4-10}$ ether or cyclic ether, $C_{3-7}$ ketone, $C_{2-6}$ ester, acetonitrile and/or benzene optionally substituted by 1-3 methyl or ethyl or halogen atoms.

In one embodiment of the present invention, the above $C_{1-6}$ alkyl alcohol is selected from methanol, ethanol, isopropanol, and/or n-butanol.

In one embodiment of the present invention, the $C_{5-10}$ alkane or cycloalkane is selected from pentane, n-hexane, n-heptane and/or cyclohexane.

In one embodiment of the present invention, the $C_{4-10}$ ether or cyclic ether is selected from methyl tert-butyl ether, tetrahydrofuran, dimethyl tetrahydrofuran and/or 1,4-dioxane.

In one embodiment of the present invention, the above $C_{3-7}$ ketone is selected from acetone, methyl isobutyl ketone, and/or methyl ethyl ketone.

In one embodiment of the present invention, the above $C_{2-4}$ ester is selected from ethyl acetate, and/or isopropyl acetate.

In one embodiment of the present invention, the benzene optionally substituted by 1-3 methyl or ethyl or halogen atoms is selected from methylbenzene, xylene, or chlorobenzene.

In one embodiment of the present invention, the mixed solvent of organic solvent and water is selected from methanol/water, ethanol/water, isopropanol/water, acetonitrile/water, acetone/water, tetrahydrofuran/water or 1,4-dioxane/water.

In one embodiment of the present invention, the volume ratio of organic solvent to water is 0.1-20:1.

In some embodiments of the present invention, the organic solvent is selected from isopropanol, acetonitrile, methyl isobutyl ketone, ethyl acetate, isopropyl acetate, dimethyl tetrahydrofuran, toluene, and/or methanol.

In one embodiment of the present invention, the volume ratio of organic solvent to water is specifically 0.5-5:1.

The present invention also provides crystal form IV of compound 5-3, the structure of which is shown in FIG. 3.

In one embodiment of the present invention, the XRPD pattern analysis of crystal form IV is as follows.

| diffraction angle 2θ | relative intensity (%) |
|---|---|
| 8.653 | 100.0 |
| 10.408 | 94.7 |

-continued

| diffraction angle 2θ | relative intensity (%) |
|---|---|
| 12.106 | 45.5 |
| 12.362 | 15.5 |
| 13.723 | 14.5 |
| 14.152 | 6.1 |
| 14.414 | 7.3 |
| 14.925 | 10.6 |
| 15.988 | 18.9 |
| 16.682 | 20.1 |
| 16.937 | 33.6 |
| 17.311 | 79.1 |
| 17.982 | 61.7 |
| 18.338 | 29.2 |
| 19.245 | 5.9 |
| 19.856 | 29.2 |
| 20.721 | 24.1 |
| 21.020 | 8.2 |
| 21.611 | 34.8 |
| 23.385 | 22.1 |
| 23.997 | 44.0 |
| 24.430 | 30.5 |
| 24.965 | 15.2 |
| 26.225 | 9.3 |
| 26.562 | 23.9 |
| 26.977 | 6.8 |
| 27.647 | 16.3 |
| 27.983 | 10.9 |
| 29.659 | 3.1 |
| 30.842 | 3.0 |
| 31.788 | 12.4 |
| 33.031 | 2.7 |
| 33.426 | 2.2 |
| 33.858 | 2.8 |
| 34.884 | 2.3 |
| 36.499 | 4.8 |
| 37.427 | 2.9 |

The present invention also provides a method for preparing crystal form IV, which comprises that adding crystal form I of compound 5-3 or any other form of compound 5-3 except crystal form II into a polar organic solvent, dissolving at room temperature or heating to a temperature of 40° C. to reflux temperature for dissolution, then slowly adding a weak polar or non-polar organic solvent dropwise, and after the addition is completed, forming the crystal at room temperature or by cooling to 20-30° C. in 1-120 hours.

In one embodiment of the present invention, the above organic solvent is selected from $C_{1-6}$ alkyl alcohol, $C_{5-10}$ alkane or cycloalkane, $C_{4-10}$ ether or cyclic ether, $C_{3-7}$ ketone, $C_{2-6}$ ester, acetonitrile and/or benzene optionally substituted by 1-3 methyl or ethyl or halogen atoms.

In one embodiment of the present invention, the above $C_{1-6}$ alkyl alcohol is selected from methanol, ethanol, isopropanol, and/or n-butanol.

In one embodiment of the present invention, the $C_{5-10}$ alkane or cycloalkane is selected from pentane, n-hexane, n-heptane and/or cyclohexane.

In one embodiment of the present invention, the above $C_{4-10}$ ether or cyclic ether is selected from methyl tert-butyl ether, tetrahydrofuran, dimethyl tetrahydrofuran and/or 1,4-dioxane.

In one embodiment of the present invention, the above $C_{3-7}$ ketone is selected from acetone, methyl isobutyl ketone, and/or methyl ethyl ketone.

In one embodiment of the present invention, the above $C_{2-6}$ ester is selected from ethyl acetate, and/or isopropyl acetate.

In one embodiment of the present invention, the benzene optionally substituted by 1-3 methyl or ethyl or halogen atoms is selected from methylbenzene, xylene, or chlorobenzene.

In one embodiment of the present invention, the mixed solvent of organic solvent and water is selected from methanol/water, ethanol/water, isopropanol/water, acetonitrile/water, acetone/water, tetrahydrofuran/water or 1,4-dioxane/water.

In one embodiment of the present invention, the volume ratio of organic solvent to water is 0.1-20:1.

In some embodiments of the present invention, the organic solvent is specifically selected from isopropanol, acetonitrile, methyl isobutyl ketone, ethyl acetate, isopropyl acetate, dimethyl tetrahydrofuran, toluene, and/or methanol.

In one embodiment of the present invention, the volume ratio of organic solvent to water is specifically 0.5-5:1.

Another object of the present invention is to provide a use of crystal form I or crystal form II or crystal form III or crystal form IV of compound 5-3 as orexin receptor antagonist in the manufacture of a medicament for the treatment or prevention of neurological and psychiatric disorders or orexin-related diseases.

In one embodiment of the present invention, the above mentioned use of crystal form I or crystal form II or crystal form III or crystal form IV of compound 5-3 as orexin receptor antagonist in the manufacture of a medicament for the treatment or prevention of neurological and psychiatric disorders or orexin-related diseases, wherein the neurological and psychiatric disorders or orexin-related diseases include insomnia, chronic obstructive pulmonary disease, obstructive sleep apnea, hypersomnia, anxiety, obsessive-compulsive disorder, panic attack, nicotine addiction, or binge eating disorder.

Definition and Description

Unless otherwise stated, the following terms and phrases used herein are intended to have the following meanings. A particular term or phrase should not be considered as indefinite or unclear unless it is specifically defined and should be understood in accordance with the ordinary meaning.

When a trade name appears in this article, it is intended to refer to its corresponding product or its active ingredient.

$C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$.

The term "substituted" refers to any one or more hydrogen atom on particular atoms is (are) substituted by a substituent, including deuterium and variants of hydrogen, as long as the particular atom is of normal valence and the compound is stable after substitution. When a substituent is ketone group (i.e., =O), it means that two hydrogen atoms are replaced. Ketone group substitution does not occur on the aromatic group. The term "optionally substituted" means that it may be substituted, or may be unsubstituted. Unless otherwise specified, the type and number of substituents may be arbitrary as long as it is chemically achievable.

When any variable (e.g., R) occurs more than once in the composition or structure of the compound, its definition in each case are independent. Thus, for example, if a group is substituted with 0-2 of R, then the group may optionally be substituted with up to two R, and R in each case can be independent. In addition, the combination of substituents and/or the variants thereof is allowed only if such combination results in a stable compound.

Unless otherwise specified, the term "halogen element" or "halogen" by itself or as a part of another substituent denotes fluorine, chlorine, bromine or iodine atom. Furthermore, the term "haloalkyl" means to include monohaloalkyl and polyhaloalkyl. For example, the term "halo (C1-C4) alkyl" is intended to include, but not limited to, trifluoromethyl, 2,2,2-trifluoroethyl, 4-chlorobutyl and 3-bromopropyl and the like.

The term "halogen" or "halo" refers to fluorine, chlorine, bromine and iodine.

Unless otherwise specified, "ring" represents a substituted or unsubstituted cycloalkyl, heterocycloalkyl, cycloalkenyl, heterocycloalkenyl, cycloalkynyl, heterocycloalkynyl, aryl, or heteroaryl. The ring includes a monocyclic ring, bicyclic ring, spiro ring, fused ring or bridge ring. The number of ring atoms is usually defined as the member number in a ring, for example, "5 to 7-membered ring" means 5 to 7 atoms are arranged in a cycle. Unless otherwise specified, the ring optionally contains 1 to 3 hetero atoms. Therefore, "5 to 7-membered ring" includes for example, phenyl pyridine and piperidinyl; on the other hand, the term "5 to 7-membered heterocycloalkyl ring" include pyridyl and piperidyl, but excluding phenyl. The term "ring" also includes ring systems containing at least one ring, wherein each "ring" independently meets the above definition.

Unless otherwise specified, the term "hydrocarbyl" or the specific concept (such as alkyl, alkenyl, alkynyl, phenyl, etc.) by itself or as a part of another substituent represents a straight, branched or cyclic hydrocarbon radical or combinations thereof, may be fully saturated, mono- or poly-unsaturated, may be mono-, di- or poly-substituted, can be monovalent (eg methyl), divalent (eg methylene) or polyvalent (eg methine), and may include divalent or multivalent radicals, and has certain number of carbon atoms (for example, C1-C10 indicates 1 to 10 carbons). "Hydrocarbyl" includes but not limited to aliphatic hydrocarbon groups and aromatic hydrocarbon groups. The aliphatic hydrocarbon groups include linear and cyclic groups, and include but are not limited to alkyl group, alkenyl group, and alkynyl group; the aromatic hydrocarbon groups include but are not limited to 6-12 membered aromatic hydrocarbon groups, such as benzene, naphthalene and the like. In some embodiments, the term "alkyl" represents linear, branched radicals or the combinations thereof, which may be fully saturated, mono- or poly-unsaturated and can include di- or multivalent radicals. Examples of saturated hydrocarbon radicals include, but are not limited to, methyl, ethyl, n-propyl, isopropyl, n-butyl, tertiary butyl, isobutyl, sec-butyl, isobutyl, cyclohexyl, (cyclohexyl) methyl, cyclopropylmethyl, and homologs or isomers of n-pentyl, n-hexyl, n-heptyl, n-octyl radicals. Unsaturated alkyl groups have one or more double or triple bonds, examples of which include but are not limited to, ethenyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and higher homologs and isomers.

Unless otherwise specified, the term "heterohydrocarbyl", or the specific concepts thereof (e.g. heteroalkyl, heteroalkenyl, heteroalkynyl, heteroaryl, etc.) by itself or in combination with other terms indicates a stable straight chain, branched chain or cyclic hydrocarbon radical, or the combinations thereof and comprises a certain number of carbon atoms and at least one hetero atoms. In some embodiments, the term "heteroalkyl" by itself or in combination with other terms indicates a stable straight chain, branched chain, or the combinations thereof and comprises a certain number of carbon atoms and at least one hetero atoms. In one exemplary embodiment, a heteroatom is selected from B, O, N and S, wherein the nitrogen and sulfur atoms are optionally oxidized and the nitrogen atom is optionally quaternized. Heteroatoms B, O, N and S may be located on any interior position of heterohydrocarbyl (include the positions on which the hydrocarbon group attached to the remainder of the molecule). Embodiments comprise but are not limited to —CH$_2$—CH$_2$O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —CH$_2$—CH=N—OCH$_3$ and —CH=CH—N(CH$_3$)—CH$_3$. Up to two heteroatoms may be consecutive, such as —CH$_2$—NH—OCH$_3$.

Unless otherwise specified, the terms "cycloalkyl", "heterocycloalkyl" or a specific concept thereof (such as aryl, heteroaryl, cycloalkyl, heterocycloalkyl, cycloalkenyl, heterocycloalkenyl, cycloalkynyl, heterocycloalkynyl, etc.) by itself or in combination with other terms represent, respectively, a cyclized "hydrocarbon group", "heterohydrocarbyl". In addition, for heterohydrocarbyl or heterocycloalkyl (such as heteroalkyl, heterocycloalkyl), the heteroatom may occupy the position at which the heterocycle is attached to the rest of the molecule. Examples of cycloalkyl include, but are not limited to, cyclopentyl, cyclohexyl, 1-cyclohexenyl, 3-cyclohexenyl, cycloheptyl and the like. Non-limiting examples of heterocyclic group include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuranindole-3-yl, tetrahydrothien-2-yl, tetrahydrothien-3-yl, 1-piperazinyl and 2-piperazinyl.

The compounds of the present invention may be prepared by various synthetic methods well known to those skilled in the art, including the specific embodiments enumerated below, embodiments in conjunction with other methods of chemical synthesis, and the equivalents familiar for the skilled in the art. The preferred embodiments include but are not limited to the examples of the present invention.

The solvents used in the present invention are commercially available, and can be used without further purification.

Compounds are named manually or with ChemDraw® software, and commercial compounds are available under Supplier directory name.

The X-ray powder diffraction method is as follows:

Instrument: Bruker D8 ADVANCE X-ray diffractometer; Target: Cu: K-Alpha; Wavelength λ=1.54179Å; Tube Voltage: 40 kV; Tube Current: 40 mA; Scanning Range: 4-40; Sample Rotation Speed: 15 rpm; Scanning Speed: 10°/min. Unless otherwise specified, the following abbreviations are used herein: SGF represents simulated gastric fluid; Fassif represents simulated intestinal fluid in fasting state; LDA represents lithium diisopropylamide; MsCl represents methanesulfonyl chloride; BOC represents t-butylcarbonyl as an amine protecting group; THF represents tetrahydrofuran; rt represents room temperature; DCM represents dichloromethane; TEA represents triethylamine; DMF represents N,N-dimethylformamide; DBU represents 1,8-diazabicycloundec-7-ene; LAH represents lithium aluminum hydride; HATU represents 2-(7-azobenzotriazole)-N,N,N',N'-tetramethyluronium hexafluorophosphate; CDI represents carbonyldiimidazole; DMSO represents dimethylsulfoxide; MeOH represents methanol; EtOH represents ethanol; EtOAc represents ethyl acetate; THF represents tetrahydrofuran; IPA represents isopropanol; ACN represents acetonitrile; MEK represents butanone; MIBK represents methyl isobutyl ketone; MTBE represents methyl tert-butyl ether; DPBS represents DuPont phosphate buffer solution; T3P represents propyl phosphoric anhydride; EDCI represents 1-ethyl-3-(3-dimethylaminopropyl)carbodiimide; HOBt represents 1-hydroxybenzotriazole.

DETAILED DESCRIPTION

Figure 1:
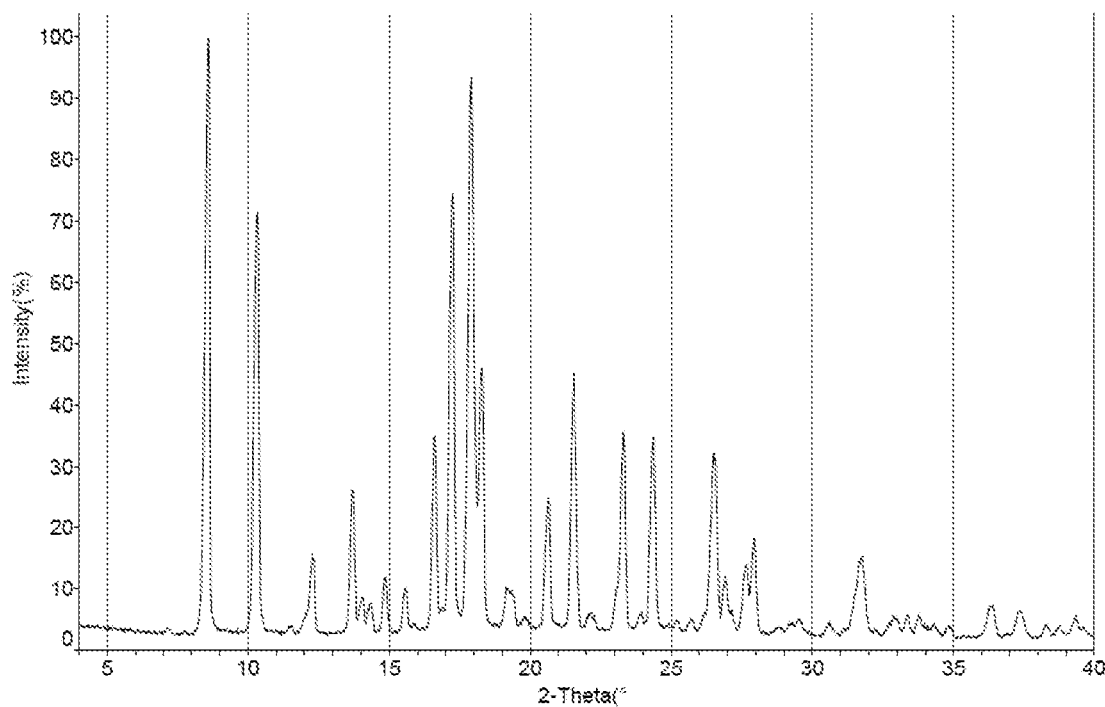
FIG. 1 is a XRPD pattern of Cu—K alpha radiation for crystal form I of compound 5-3.
Figure 2:
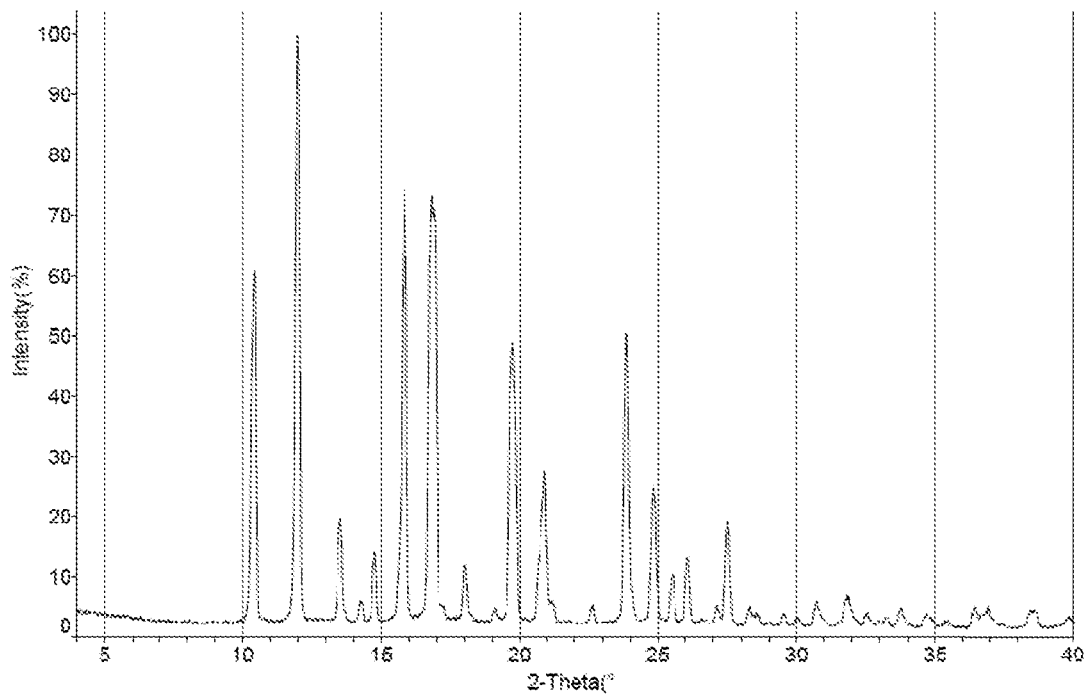
FIG. 2 is a XRPD pattern of Cu—K alpha radiation for crystal form II of compound 5-3.
Figure 3:
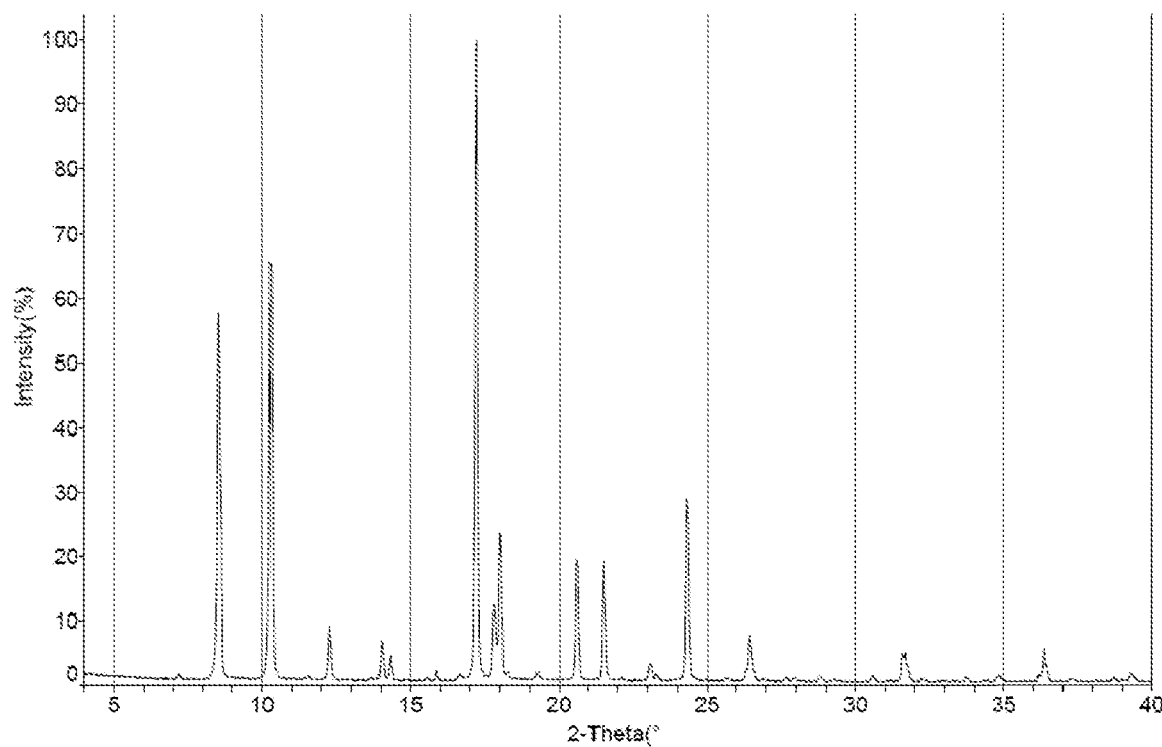
FIG. 3 is a XRPD pattern of Cu—K alpha radiation for crystal form III of compound 5-3.

The present invention will be further illustrated below with reference to the specific examples, but these examples are not to make any disadvantage limitation to the invention. This invention has been described in detail herein, and the embodiments for carrying out the invention are disclosed. It would be obvious for those skilled in the art can to make various changes and modifications to the embodiments for carrying out the present invention without departing from the spirit and scope of the present invention.

Example 1: Preparation of Compound 1

Step 1: Preparation of Compound 3

22 liters of anhydrous toluene were added to a 50 liters reactor, sodium hydrogen (2.2 Kg, 55.5 mol) was added slowly into the toluene solution in batches under the protection of nitrogen, and compound 2 (3.93 Kg, 33.3 mol) was dropped into the reactor at the same time. The compound 1 (5.0 Kg, 22.2 mol) was dissolved in toluene (9 L) in a flask. The reactor was heated to 85-95° C., and the toluene solution of compound 1 prepared was added slowly to the reactor within about 2 hours. Pay attention to the dripping rate and controlled the temperature at about 95° C. After the addition was completed, the solution was stirred for another 0.5-1 hour at this temperature, and then some samples were taken and quenched by water. The upper organic phase was checked by TLC and the reaction was complete.

The reaction solution was cooled to about 60° C., and the viscous reaction solution was released while heat, and was poured into a mixed solution of 66 liters of ice water, 32.5

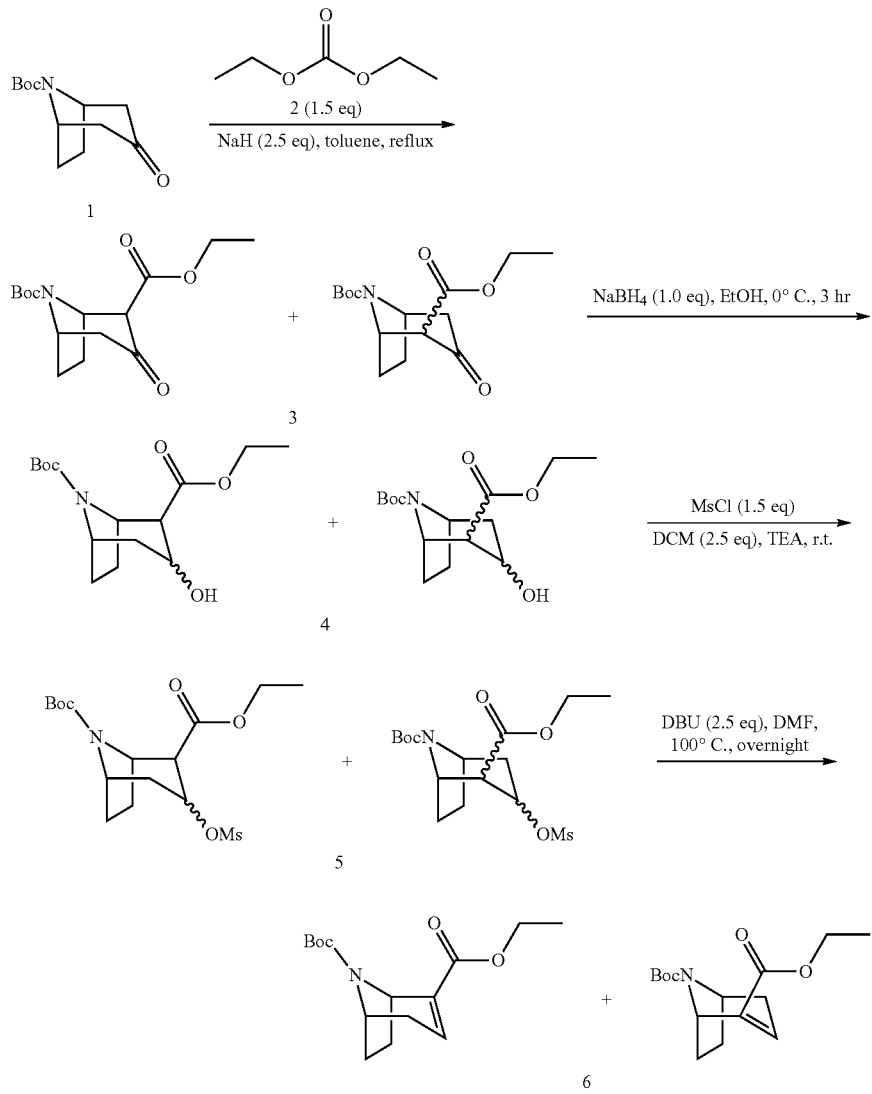

liters of ethyl acetate and 4.65 liters of hydrochloric acid to quench the reaction. The corresponding additional ice was supplemented to control temperature below 10° C. during stirring. After the quench was completed, the layer was statically separated, and the aqueous phase was extracted with 10 liters of ethyl acetate, and the combined organic phase was washed with 11 liters of saturated brine. The washed organic phase was dried over 2.8 Kg of anhydrous sodium sulfate. After filtration, the product solution was concentrated at 55° C. under reduced pressure (−0.09 Mpa) to give 7.25 Kg crude product which was used for the next step directly without further purification.

Step 2: Preparation of Compound 4

In a 50 liter reactor, 7.25 Kg of crude compound 3 was dissolved in 32 liters of ethanol, and then cooled to 0-5° C. Sodium borohydride (843.6 g, 22.2 mol) was added to the reactor in batches, and controlled the speed of adding and made the temperature below 10° C., this took 0.5-1.5 hours. After the addition was completed, stirring was continued at 0-10° C. for 2-3 hours. Samples were taken and monitored, TLC (ethyl acetate/petroleum ether=1/3, high temperature coloration of ninhydrin) showed that the reaction was completed.

The temperature was controlled below 10° C., and the hydrochloric acid (11.1 L, 2M) was slowly dripped into the reactor to adjust pH to 6-7. After quenching, the reaction mixture was concentrated directly under reduced pressure (−0.09 Mpa, <55° C.) to remove most of the ethanol. The concentrated mixture solution was extracted with ethyl acetate two times (11 L×2), and the organic phase was combined and washed with saturated brine (5.5 L), dried over anhydrous sodium sulfate (2.2 Kg) and filtered. The product solution was concentrated under reduced pressure (−0.09 Mpa, <55° C.) to give the oily crude product which was directly used for the next step without purification.

Step 3: Preparation of Compound 5

In a 50 liter reactor (50 L), compound 4 (6.82 Kg, 22.2 mol, crude) was dissolved in dichloromethane (30 L), and triethylamine (5.80 Kg, 57.3 mol) was added. The temperature was cooled below 10° C., and the methanesulfonyl chloride (3.82 Kg, 33.3 mol) was slowly dripped into the reactor, kept the temperature below 15° C. for 1-2 hours. The reaction solution was heated to 25° C. and stirred for 16 hours, samples were taken. TLC (ethyl acetate/petroleum ether=1/3, high temperature coloration of ninhydrin) showed that compound 4 disappeared and the reaction was completed.

The reaction solution was washed with water (11 L) twice, and then washed with dilute hydrochloric acid (about 7 L, 2M). Controlled the aqueous phase pH=6-8, and then washed with saturated brine (11 Kg), and dried over anhydrous sodium sulfate (1.57 Kg) finally, filtered to give the product solution, concentrated (−0.09 Mpa, <55° C.) to obtain the crude product which was directly used for the next step without purification.

Step 4: Preparation of Compound 6

In a 50 liter reactor, compound 5 (9.4 Kg, crude, 22.2 mol) was dissolved in DMF (22 L), and the temperature was controlled below 40° C. DBU (6.76 Kg, 44.4 mol) was added to the reactor. After the addition was completed, the temperature was raised to 100° C. and stirred for 16-20 hours. Samples were taken, TLC showed that compound 5 disappeared and the reaction was completed.

The reaction solution was cooled to 25° C. Water (22 L) and ethyl acetate (33 L) were then added and stirred for 10 minutes. The liquid was layered, which the aqueous phase was extracted with ethyl acetate (22 L). The organic phase was combined, and washed with 0.5N hydrochloric acid solution (15 L) (controlled the aqueous phase pH=6-7), the organic phase was washed with water (22 L) again. It was then dried over and filtered with anhydrous sodium sulfate (2.2 Kg). The solution was mixed with silica gel, and concentrated (−0.09 Mpa, <55 C) to dryness to get the crude product which was purified by the column (eluent: ethyl acetate/n-heptane=1/20) to get the pure product compound 6 (2.80 Kg, the total yield of four steps: 44.9%). $^1$HNMR (CDCl$_3$, 400 MHz) δ 6.69 (s, 1H), 4.75 (s, 1H), 4.30 (s, 1H), 4.16 (d, J=6.4 Hz, 2H), 2.81 (bs, 1H), 2.12 (m, 1H), 2.02 (m, 1H), 1.92 (m, 1H), 1.62 (m, 1H), 1.41 (s, 9H), 1.24 (t, J=7.2 Hz, 3H).

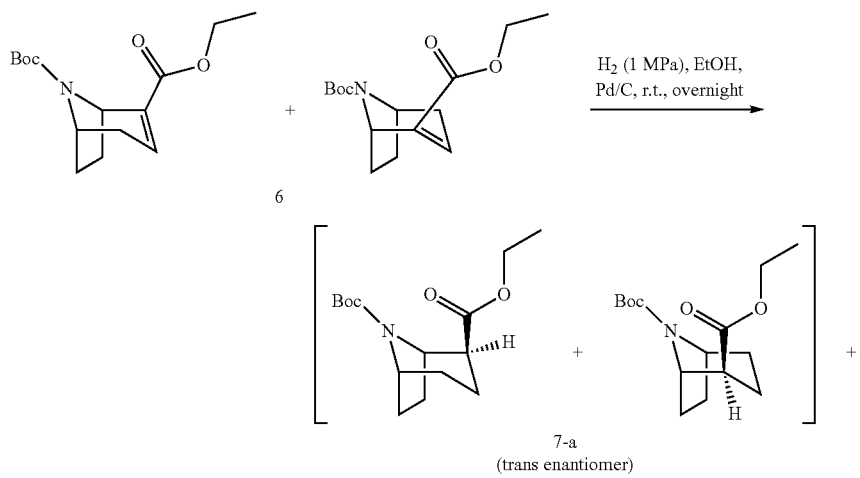

Scheme 2

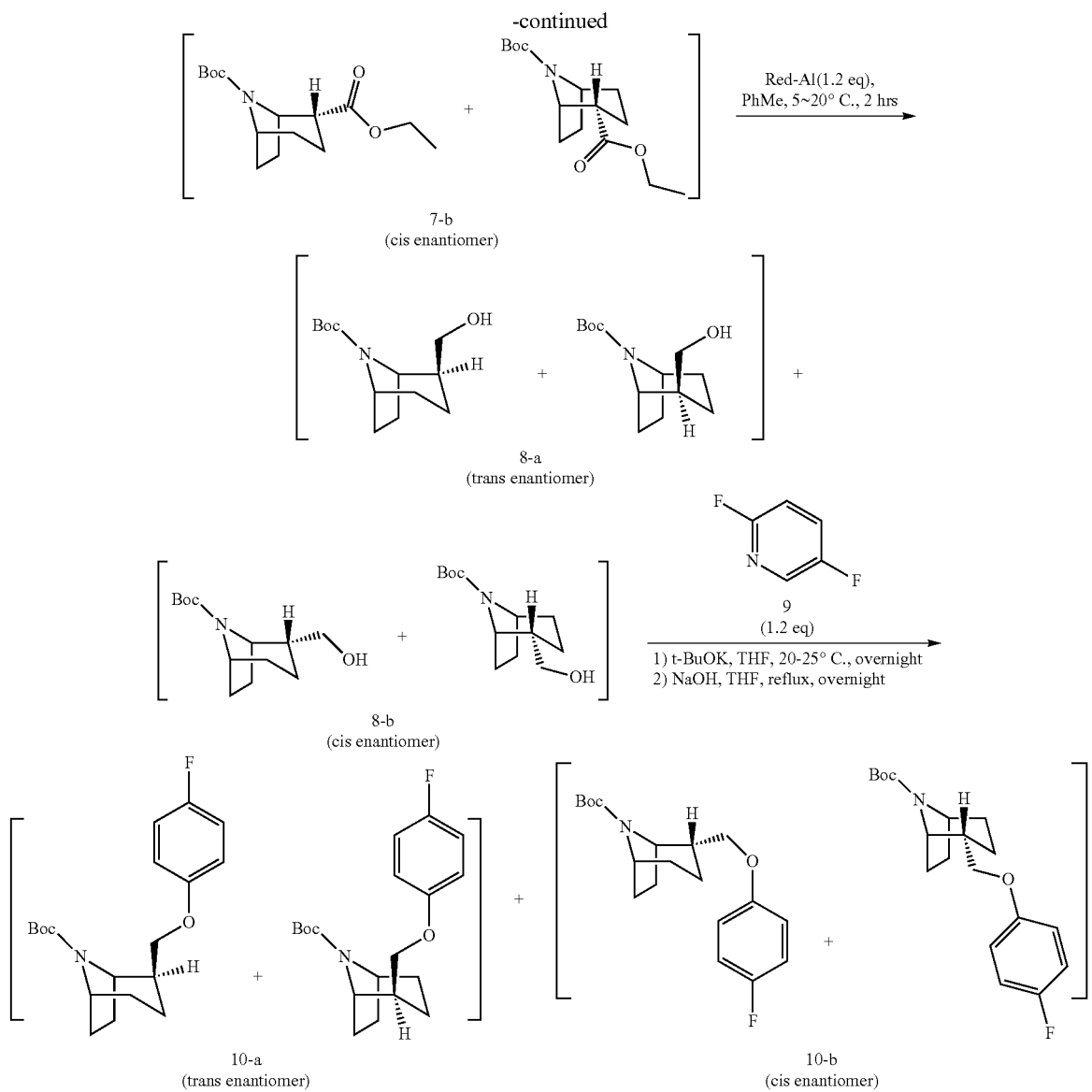

Step 5: Preparation of Compound 7-a and 7-b

Ethanol (1 L) was added to a 10 L autoclave, and the wet Pd/C (170 g) was slowly added into the autoclave for one time under the argon protection. Compound 6 (563 g, 2.0 mol) was dissolved in ethanol (4.63 L) and added to the autoclave. After the addition was completed, the reaction system was sealed, evacuated, and replaced with hydrogen twice and then hydrogen was introduced. The initial pressure of hydrogen in the reaction system was controlled under 4.0 Mpa, stirred overnight at 10-15° C. Samples were taken, and the reaction was monitored by TLC or HPLC.

The reaction mixture was filtered through celite. The filter cake was washed with ethanol (I L*2, 0.79 Kg*2). The filtrate was combined, concentrated under reduced pressure to give the product compounds 7-a, 7-b (552 g, 7-a/7-b=3:1, yield: 97.5%). The product was used directly for the next step without purification.

Step 6: Preparation of Compound 8-a and 8-b

In a reactor (50 L), compound 7-a, 7-b (4.2 Kg, 7-a/7-b=3:1, 14.8 mol) was dissolved in anhydrous toluene (20 L), the reaction temperature was controlled between 0-5° C. The red aluminum (5.1 Kg, 17.8 mol) was slowly added to the reactor under stirring, and the temperature was kept between 0-5° C. for about 1 hour. After the addition was completed, stirring was continued for 1 hour at 0-5° C. Samples were taken, TLC (ethyl acetate/petroleum ether=1/3, high temperature coloration) and GC monitoring showed that the reaction was completed.

The temperature was controlled at 0-5° C. 15% sodium hydroxide solution (9 L), water (4.5 L) were added slowly to the reaction solution. The temperature was raised to 15° C. and stirred for 20 minutes. The aqueous phase of the system was extracted by toluene (10 L). The organic phase was combined and washed with water (10 L), and then dried over anhydrous sodium sulfate (1 Kg) finally. The product solution was obtained by filtration and concentrated under reduced pressure to get compound 8-a and 8-b (3.525 Kg, yield: 98.7%). The compound was used directly for the next step without purification. ¹HNMR (CDCl₃, 400 MHz) δ4.35 (m, 1H), 4.13 (m, 1H), 3.47 (m, 1H), 2.05 (m, 1H), 1.82 (m, 1H), 1.73 (m, 2H), 1.67 (m, 3H), 1.45 (s, 9H), 1.28 (m, 2H).

Step 7: Preparation of Compound 10-a and 10-b

In a 50 L reactor, compound 8-a and 8-b (3.425 Kg) were dissolved in tetrahydrofuran (17 L), and sodium hydroxide (1.136 Kg) and compound 9 (1.960 Kg) were added to the reactor. Controlled the temperature under 75° C. and stirred for 24 hours. Samples were taken, GC and TLC (ethyl acetate/petroleum ether=1/3, high temperature coloration of phosphomolybdic acid) detected that the raw materials reacted completely.

The reaction solution was cooled to room temperature, and the saturated brine (8.5 L) was added into the solution. Stirring was continued for 5 minutes. The mixture was separated. The organic phase was adjusted to pH 6-7 with 2.0 N hydrochloric acid. The mixture was separated. The aqueous phase was combined, and adjusted to pH 6-7 with 2.0 N hydrochloric acid, and extracted with ethyl acetate (10 L). The organic phase was combined and dried over anhydrous sodium sulfate (1 Kg) and filtered. The product solution was concentrated under reduced pressure (−0.09 Mpa, <55° C.) to get the crude product which was purified by silica gel column chromatography (n-heptane:ethyl acetate=20:1 to 5:1) to get a light yellow oily product (4.5 Kg yield 92.9%). ¹HNMR (CDCl₃, 400 MHz) δ7.95 (s, 1H), 7.32 (m, 1H), 6.69 (m, 1H), 4.38 (m, 2.5H), 4.13 (m, 1.5H), 2.03 (m, 3H), 1.86 (m, 3H), 1.45 (m, 3H), 1.26 (s, 9H).

Scheme 3

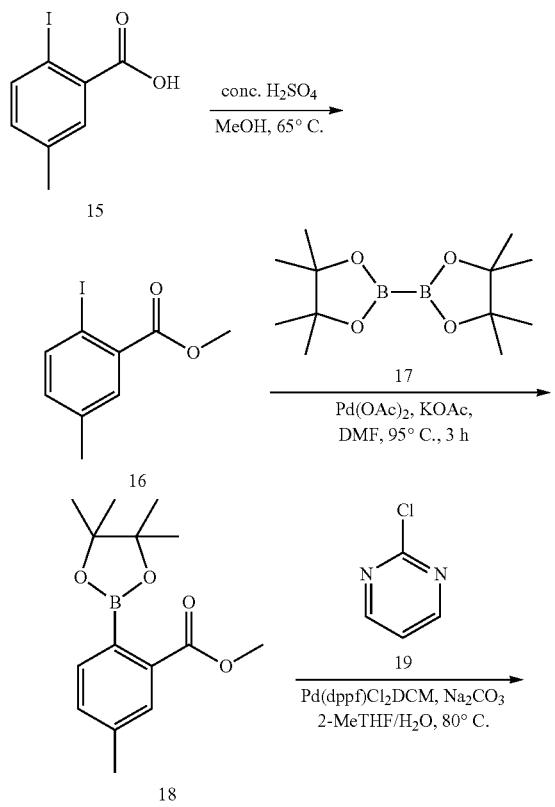

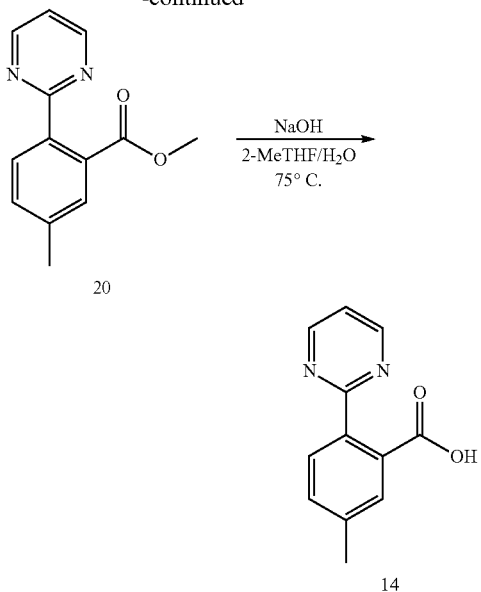

Step 8: Preparation of Compound 16

In a reactor, compound 15 (2.5 Kg, 9.54 mol) was dissolved in anhydrous methanol (10 L), and the concentrated sulfuric acid (360 mL, 7.16 mol) was slowly dripped into the reactor at room temperature. The reactor was heated to 65-80° C., and reacted for 18 hours. HPLC monitored that 5-7% of raw materials still remained. The reaction was supplemented with concentrated sulfuric acid (36 mL, 67.3 g) and continued to react for 18 hours. HPLC detected that the raw materials reacted completely.

The reaction solution was cooled to 26° C. (four-pot reactions merged for treatment), and 10N sodium hydroxide solution (3.75 L) was slowly added to adjust pH to 5-6. The reaction solution was concentrated to about 35 L, and ethyl acetate (20 L), water (8 L), and 7% of sodium bicarbonate (10 L) were added into the reaction solution. Stirred and separated, the aqueous phase was extracted again with ethyl acetate (20 L), the organic phase was combined and washed with saturated brine (15 L), and dried over anhydrous sodium sulfate. The product solution was concentrated (−0.09 MPa, <55° C.) to obtain 2.5 Kg of product (yield: 95%) which was directly used for the next step without purification. ¹HNMR (DMSO-d6, 400 MHz) δ7.76 (d, J=8.4 Hz, 1H), 7.45 (s, 1H), 6.98 (d, J=8.0, 2.5H), 3.77 (s, 3H), 2.19 (s, 3H).

Step 9: Preparation of Compound 18

First, compound 16 (5 Kg, 18.1 mol), compound 17 (4.83 Kg, 19.0 mol) and potassium acetate (4.44 Kg, 45.3 mol) were added to a reactor, and then anhydrous DMF (20 L) was added to the reactor. Stirred and dissolved at room temperature. Palladium acetate (122 g, 54.33 mmol) was added under the protection of nitrogen, the reactor was heated to 80-90° C., the reaction was stirred for 16 hours. Samples were taken, TLC (ethyl acetate/petroleum ether=1/10, UV 254 nm) and HPLC detected that the material 16 reacted completely.

The reaction solution was cooled to room temperature (25-34° C.), then filtered through celite, and washed with ethyl acetate (post-processing of two-pot reactions merged at this step). The filtrate was added ethyl acetate and water, stirred and separated. The organic phase was washed with sodium bicarbonate solution (5 L, 8%) and saturated brine (5 L) respectively, dried over anhydrous sodium sulfate (3 Kg) finally, filtered, and the product solution was concentrated to get 8 Kg of crude product (yield: 80%) which was used directly for the next step without purification.

Step 10: Preparation of Compound 20

First, compounds 18 (4 Kg, crude, 14.485 mol), compound 19 (1.74 Kg, 15.2 mol), and sodium carbonate (3.5 Kg, 33 mol) were added to a 50 L reactor, and then 2-methyl tetrahydrofuran (25 L) and water (8 L) were added to the reactor, stirred and dissolved at room temperature. Pd (dppf) Cl$_2$.DCM (325 g, 0.398 mol) was added under the protection of nitrogen, the reactor was heated to 70-80° C., and the reaction was stirred for 16 hours. Samples were taken for monitoring: TlC (ethyl acetate/petroleum ether=1/2) showed that the raw materials reacted completely.

The reaction solution was cooled to room temperature (30° C.), water (10 L) was added and stirred for 10 minutes. The mixture was separated. The aqueous phase was filtered through celite and extracted with ethyl acetate (10 L). The organic phase was combined, activated carbon powder (2.3 Kg) was added, and stirred for 2 hours (two-pot reactions merged at this step). The filtrate was filtered through celite and concentrated (<50° C.) until solid precipitation, filtered to get a black solid. The solid was dissolved in ethyl acetate (3-5 L) and filtered by silica gel column, washed with ethyl acetate, and concentrated to get compound 20 (3.0 Kg, yield: 45.5%).

Palladium Removal Process:

Compound 20 (3.0 Kg) was added to a reactor, dichloromethane (12 L) was added, stirred and dissolved at room temperature (25-27° C.). Sodium chloride (210 g), thiocyanuric acid (27 g), ammonium hydroxide (225 mL), water (2500 mL) and ethanol (to 2400 mL) were formulated into TMT solution (~5 L). The TMT solution (~5 L) was added to the reactor, and the reaction mixture was stirred at room temperature (20-25° C.) for 24 hours. The reaction solution was filtered through celite, the aqueous phase was separated and removed, and the organic phase was concentrated to dryness (−0.09 Mpa, <50° C.) to get the compound 20 (2.92 Kg, yield: 97.3%). $^1$HNMR (DMSO-d6, 400 MHz) δ8.87 (d, J=4.8 Hz, 2H), 7.96 (d, J=8.0 Hz, 1H), 7.46 (m, 3H), 3.62 (s, 3H), 2.41 (s, 3H).

Step 11: Preparation of Compound 14

In a 50 L reactor, compound 20 (2900 g, 12.7 mol) was dissolved in 2-methyl tetrahydrofuran (15 L). The sodium hydroxide solution (NaOH: 1270 g, 31.8 mol; water: 20 L, 20 Kg) was prepared, and added to the reactor, the reaction solution was heated to 70-75° C. and stirred for 16 hours, TLC (ethyl acetate/petroleum ether=1/2, UV: 254 nm) detection showed that the reaction finished.

Cooled, and the aqueous phase was separated and washed with ethyl acetate (10 L). The temperature of aqueous phase was controlled below 20° C., 12N hydrochloric acid (3.3 L) was slowly added to adjust pH to 1. The temperature was kept less than 30° C. In this process, the solid was precipitated, stirred for about 10 minutes, filtered, the filter cake was rinsed with water (5 L*2). The filtered solid was dried in vacuum to get the product compound 14 (2600 g, purity: 99%, yield: 95.6%). $^1$HNMR (DMSO-d6, 400 MHz) δ12.67 (br, s, 1H), 8.85 (d, J=4.0 Hz, 2H), 7.81 (d, J=7.6 Hz, 1H), 7.48 (s, 1H), 7.43 (m, 2H), 2.40 (s, 3H).

Scheme 4

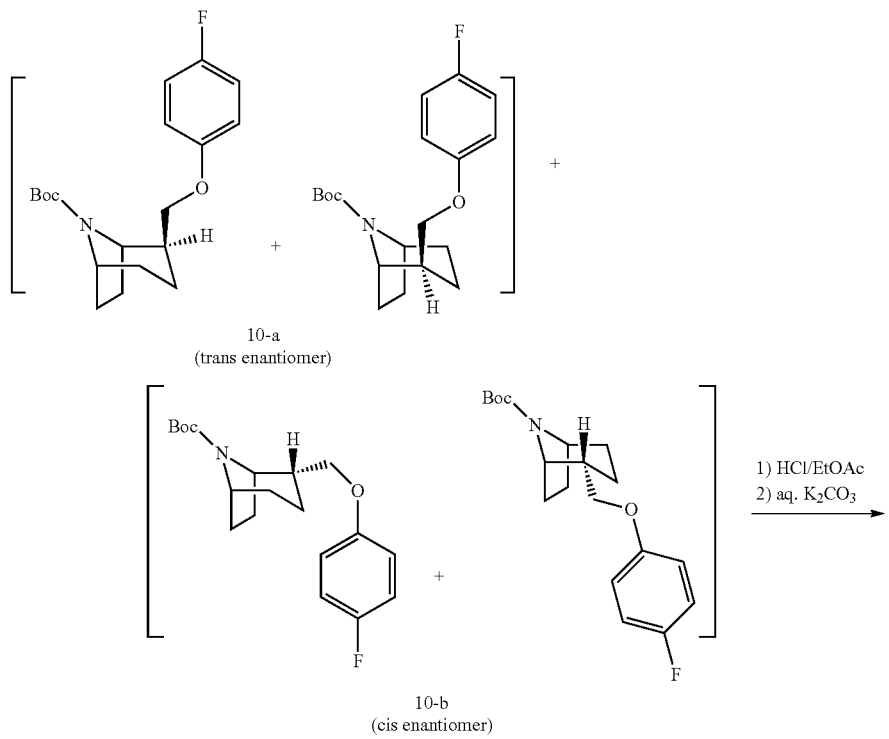

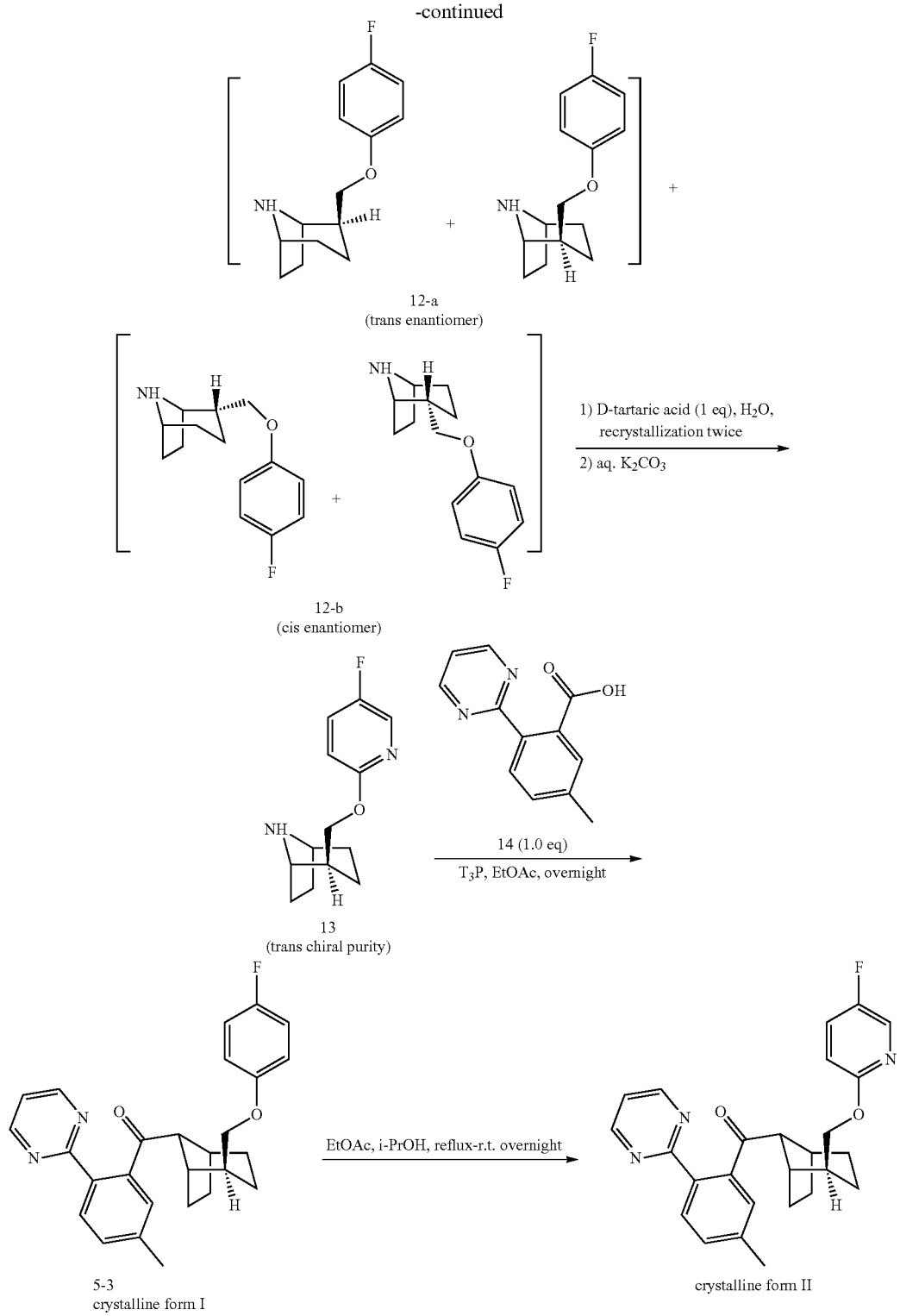

12-a
(trans enantiomer)

12-b
(cis enantiomer)

1) D-tartaric acid (1 eq), H$_2$O, recrystallization twice
2) aq. K$_2$CO$_3$ 13
(trans chiral purity)

14 (1.0 eq)
T$_3$P, EtOAc, overnight 5-3
crystalline form I

EtOAc, i-PrOH, reflux-r.t. overnight crystalline form II

Step 12: Preparation of Compound 12-a and 12-b

In a reactor (30 L), compounds 10-a and 10-b were dissolved in ethyl acetate (13.5 L). The temperature was controlled at 10-20° C., and 35% of concentrated hydrochloric acid (4.5 L) was added to the reactor. The temperature was controlled less than 15° C. (paid attention to control drip rate). After the addition was complete, the temperature was controlled at 20-25° C. and reacted for 16-20 hours, samples were taken for control. The HPLC test showed that the reaction was completely finished.

Water (5 L) was added and layered, the water layer was collected. The organic layer was extracted again with water (5 L). The water layer was combined, washed with ethyl acetate (5 L); the water layer was separated and cooled to below 10° C. The pH of water layer was adjusted to 14 with sodium hydroxide (3.0 Kg) (the addition speed of base was noted, controlled the inner temperature below 20° C.), the water layer was extracted with ethyl acetate (10 L+5 L) twice. The organic layer (15.5 Kg) was collected and the samples were taken for test. Purity=82.8%, Content=16.4%, the product weight was calculated: 2.54 Kg. The ethyl acetate solution containing the product was used directly for the next step without other treatment.

Step 13: Preparation of Compound 13

A solution of compound 12-a and compound 12-b (15.5 Kg, containing 2.54 Kg of compound 10) was added to the reactor, and heated to 55-65° C. A solution formulated by D-tartaric acid (1.62 Kg) and water (3.5 L) was slowly dripped into the reactor. After the addition was complete, the reaction was continued at 55-65° C. for 2-3 hours. Slowly cooled to 5-15'C and stirred overnight, filtered to obtain the wet product (5.78 Kg). The wet product and water (15 L) was added to the reactor, and heated to 80-90° C. to dissolve clearly, then slowly cooled to 15-25° C. and stirred continuously for 16-20 hours. Filtered to get the wet product (2.6 kg), samples were taken for test, e.e.=90.8%. The wet product and water (6 L) was added to the reactor, and heated to 80-90° C. to dissolve clearly, slowly cooled to 15-25° C. within 16-20 hours. Filtered to get the wet product (2.2 kg), samples were taken for test, e.e.=99.6%.

The wet product (2.2 Kg) and $H_2O$ (2 L) were added to the reactor and stirred to dissolve. The formulated $K_2CO_3$ aqueous solution ($K_2CO_3$:3.55 Kg, water: 10 L) was added slowly to the reactor, and the temperature was controlled at 15-25° C., stirred for 0.5-1 hours. The reaction solution was extracted with ethyl acetate (10 L*2), the organic phase was combined, dried over 2.0 Kg anhydrous $Na_2SO_4$ and filtered. The filtrate was concentrated to dryness (−0.09 MPa, <50° C.) to obtain a colorless oil compound 13 (1006 g) which turned into a white solid after cooling. Samples were taken for test ee=99.8%, HPLC Purity: 99.7%. The product was used directly for the next step without further treatment.

Step 14: Preparation of Compound 5-3

In a reactor, compound 13 (630 g, 2.67 mol) was dissolved in ethyl acetate (7.9 L), and compound 14 (685 g, 3.20 mol) was added to the reactor and stirred for 20 minutes, the temperature was controlled at 15-25° C., $T_3P$ (1903 mL, 3.20 mol) was slowly added, after 20-30 minutes of addition, the reaction solution was heated to 40-60° C. and stirred for 2-3 hours. Samples were taken for monitoring. HPLC showed that the ratio of raw material to product was less than 2.5%.

Cooled to 15-25° C. and $H_2O$ (7.9 L) was added, stirred for 0.5-1 hours, the organic phase was separated, and the aqueous phase was extracted with ethyl acetate (7.9 L). The organic phase was combined and washed with water (7.9 L) for one time. The solvent was evaporated under reduced pressure (−0.09 MPa, <50° C.) to get the crude compound 15 (1.3 KG). The crude compound was added to 3.0 L of ethyl acetate, slurried at room temperature and filtered to get the target compound (1.1 Kg, yield: 95.4%). HPLC Purity: 99.9%, e.e value: 100%. XRPD test showed it was crystal form I. $^1$H NMR (400 MHz, DMSO-d6)=8.83 (br. s., 2H), 8.17-8.01 (m, 2H), 7.49-7.33 (m, 3H), 6.86 (dd, J=3.5, 9.0 Hz, 1H), 6.86 (dd, J=3.5, 9.0 Hz, 1H), 4.63 (br. s., 1H), 4.43 (m, 1H), 4.11 (br. s, 1H), 3.79 (m, 1H), 2.52-2.48 (m, 2H), 2.35-1.95 (m, 8H), 1.29-1.20 (m, 2H).

Step 15: Preparation of Crystal Form II

Crystal form I (1.1 Kg), ethyl acetate (2750 mL) and isopropanol (110 mL) were added into a 5l reaction flask, the reaction system was heated to 65-80° C. and stirred for 2-3 hours, the temperature was slowly lowered to 50-60° C. within 1-2 hours, the suspension was continuously stirred at 40-50° C. for 20-24 hours. A little of samples were taken, and detected by XRPD which showed the crystal completely transformed successfully. The temperature of system was cooled to 10-20° C. slowly, and kept stirring at this temperature for 20-24 hours. The XRPD test showed that the crystal form was not changed. A solid was obtained by filtration and dried at 40-50° C. in vacuum for 20-24 hours to get the product (660 g, yield: 60%). HPLC Purity: 99.13%, ee value: 100%. The XRPD test showed it was crystal form II.

Example 2: Preparation of Crystal Form III 0.30 g of crystal form 1 of compound 5-3 was added to 4.5 ml toluene, fully dissolved and filtered, 4 ml n-heptane was gradually added to the filtrate under stirring until the solid was precipitated, continuously stirred at 20-30° C. for 16-22 hours, filtered to obtain a solid, dried under vacuum at 40° C. to get 0.22 g of crystal form III (yield: 73.3%).

Example 3: Preparation of Crystal Form IV 0.30 g of crystal form I of compound 5-3 was added to 4.5 ml ethanol, fully dissolved and filtered, 9 ml pure water was gradually added to the filtrate under stirring until the solid was precipitated, continuously stirred at 20-30° C. for 16-22 hours, filtered to obtain a solid, dried under vacuum at 40° C. to get 0.23 g of crystal form IV (yield: 76.7%).

Experimental Example 1: In Vitro Test of OX1/2R

Experimental Purpose

The inhibitive effect of a compound on OX1 and OX2 GPCR receptor was evaluated by detecting calcium signal change in cells with FLIPR, and IC50 value of compound was used as an indication.

Experimental Materials

Cell line: HEK293-OX1 and OX2 stable cell strain
HEK293-OX1 cell culture media (DMEM, Invitrogen #11960-044, 10% serum Gibco #10099141, L-Glutamine 1×, Gibco #25030, sodium pyruvate 1×, Gibco #11360, Geneticin 300 µg/ml, Gibco #10131).
HEK293-OX2 cell culture media (DMEM, Invitrogen #11960-044, 10% serum Gibco #10099141, L-Glutamine 1×, Gibco #25030, sodium pyruvate 1×, Gibco #11360, Geneticin 300 µg/ml,
Gibco #10131, Blasticin 2 µg/ml, Invitrogen #R21001).
Pancreatic enzyme (Invitrogen, #25200-072)
DPBS (Hyclone, #SH30028.01B)
Fluo-4 AM, Invitrogen #F14202
F-127, Invitrogen #P3000MP
Probenecid, Sigma #P8761
384-well cell plate, Greiner #781946
384-well compound plate, Greiner #781280

CO$_2$ incubator, Thermo #371

Centrifuge, Eppendorf #5810R

Vi-cell cytometry, Beckman Coulter

POD 810 Plate Assembler Automatic microplate pretreatment system

Labcyte FLIPR, Molecular Device.

Experimental Procedures and Methods a) Cell inoculation (HEK293-OX1 and HEK293-OX2 cells)

1) The medium, trypsin, and DPBS were preheated at 37° C. under water bath. Culture medium of cells was sucked and cells were washed with 10 mLD PBS;

2) The preheated trypsin was added into the culture bottle which was rotated so that trypsin uniformly covered the bottle. It was placed in an incubator (37° C., 5% CO$_2$) to digest for 1-2 minutes;

3) Each T150 was suspended with 10-15 mL of culture medium, and centrifuged at 800 rpm for 5 minutes. Cells were resuspended with 10 mL medium, and 1 mL of the cell re-suspension was sucked out and counted with Vi-cell cytometry.

4) The OX1 cells were diluted with culture medium to 5×10$^5$ cells/mL, and OX2 cells were diluted to 4×10$^5$ cells/mL. The diluted cells were added into 384 plate (Greiner, 781946) with multichannel pipettes (50 L/hole, OX1 cells: 25000 cells/hole; and OX2 cells: 20000 cells/hole).

The cell plate was placed in an incubator (37° C., 5% CO$_2$) overnight.

b) loading of the compound:

1) DMSO was used to dilute the compound into 20 mM by using 3-fold dilution. 8 gradients in duplicate wells were used. Echo liquid handler was used to add the compound into a compound plate. Then 20 μL buffer was added to ensure that the final DMSO concentration was 0.1%.

c) FLIPR experiment:

1) The cell culture medium in 384-well plate was washed away with a vacuum pump. 30 μL fluorescent dye Fluo4AM was added. The cell was incubated at 37° C., 5% CO$_2$ in an incubator for 1 hr and then re-equilibrated under room temperature for 10 minutes.

2) EC50 Test: Orexin A was diluted manually on ice by using 3-fold diluted. 8 gradients in duplicate wells were used. Then the DMSO plate was prepared and the DMSO concentration was 0.5%. The cell plate, Orexin A plate, and DMSO plate were placed into FLIPR respectively, and the fluorescence values were read.

3) EC70 value was calculated based on EC50 value of Orexin A. 5×EC70 solution was prepared and added into a 384-well compound plate with multichannel pipettes. The plate was placed on ice for preservation.

4) In the FLIPR, the compound plate, 5×EC70 plate, cell plate and FLIPR tips were placed respectively. The program was run and the fluorescence values were read.

d) Data Analysis: Prism5.0 was used to analysis the data, and the IC$_{50}$ value of the compound was calculated.

The experimental results are shown in table 1:

TABLE 1

| IC$_{50}$ experimental results detected in FLIPR | | |
|---|---|---|
| Test sample | hOX1R | hOX2R |
| Compound 5-3 | A | A |

Note:
A ≤ 50 nM.

Conclusion: the compound of the invention show significant inhibitory effects on OX1 and OX2 GPCR receptors.

Experimental Example 2: Solubility Test

Solubility Study of crystal form I of compound 5-3:1-1.5 mg of crystal form I of compound 5-3 was added to a flask at room temperature, a single organic solvent or a mixed solvent was added in small quantities and many times until the visual solution was clear or no solid particles were present, determined the solubility of crystal form I in different solvents, the results were shown in Table 2.

TABLE 2

The solubility of crystal form I in different solvents

| Num. | Solvent | Solubility (mg/mL) |
|---|---|---|
| 1 | MeOH | >53 |
| 2 | EtOH | 22-55 |
| 3 | IPA | 10-20 |
| 4 | n-butanol | 22-55 |
| 5 | ACN | 20-50 |
| 6 | Acetone | >52 |
| 7 | MEK | >54 |
| 8 | MIBK | 24-60 |
| 9 | EtOAc | 19-48 |
| 10 | MTBE | <1 |
| 11 | THF | >53 |
| 12 | Toluene | >54 |
| 13 | 1,4-dioxane | >57 |
| 14 | water | <1 |
| 15 | MeOH—H$_2$O (3:1) | 18-46 |

Solubility Study of crystal form II of compound 5-3:10 mg of crystal form II was added to a 1.5 mL volumetric flask at 37° C., 1 mL solvent was added, shook for 24 hours, centrifuged, and the supernatant was immediately analyzed by HPLC, the results were shown in Table 3,

TABLE 3

The solubility of crystal form II in different aqueous media

| Solvent | Appearance | Solubility (mg/mL) | Final pH | Solubility | Crystal form of residual solid |
|---|---|---|---|---|---|
| 0.1N HCl | turbid | 0.42 | 0.80 | Slightly soluble | crystal form II |
| water | turbid | 0.14 | 7.95 | Slightly soluble | crystal form II |
| Simulate gastric fluid | turbid | 0.27 | 1.88 | Slightly soluble | crystal form II |
| Simulated fasting intestinal fluid | turbid | 0.18 | 6.65 | Slightly soluble | crystal form II |

TABLE 3-continued

The solubility of crystal form II in different aqueous media

| Solvent | Appearance | Solubility (mg/mL) | Final pH | Solubility | Crystal form of residual solid |
|---|---|---|---|---|---|
| Simulated postprandial intestinal fluid | turbid | 0.29 | 5.04 | Slightly soluble | crystal form II |

What we claim:

1. A crystal of compound 5-3 as shown in formula 5-3,

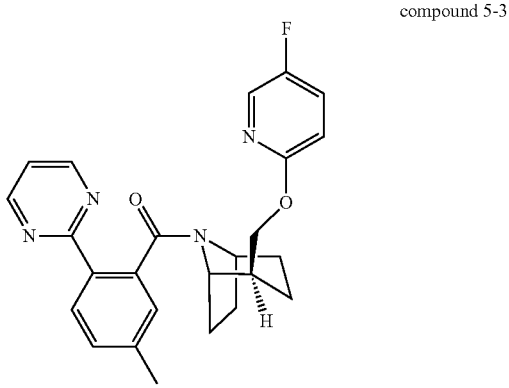 [SMILES: Cc1ccc(-c2ncccn2)c(C(=O)N2C3CCC2[C@@H](COc2ccc(F)cn2)CC3)c1]

compound 5-3 wherein the crystal is crystal form IV;
the XRPD pattern analysis of crystal form IV is as follows:

| diffraction angle 2θ | relative intensity (%) |
|---|---|
| 8.653 | 100.0 |
| 10.408 | 94.7 |
| 12.106 | 45.5 |
| 12.362 | 15.5 |
| 13.723 | 14.5 |
| 14.152 | 6.1 |
| 14.414 | 7.3 |
| 14.925 | 10.6 |
| 15.988 | 18.9 |
| 16.682 | 20.1 |
| 16.937 | 33.6 |
| 17.311 | 79.1 |
| 17.982 | 61.7 |
| 18.338 | 29.2 |
| 19.245 | 5.9 |
| 19.856 | 29.2 |
| 20.721 | 24.1 |
| 21.020 | 8.2 |
| 21.611 | 34.8 |
| 23.385 | 22.1 |
| 23.997 | 44.0 |
| 24.430 | 30.5 |
| 24.965 | 15.2 |
| 26.225 | 9.3 |
| 26.562 | 23.9 |
| 26.977 | 6.8 |
| 27.647 | 16.3 |
| 27.983 | 10.9 |
| 29.659 | 3.1 |
| 30.842 | 3.0 |
| 31.788 | 12.4 |
| 33.031 | 2.7 |
| 33.426 | 2.2 |
| 33.858 | 2.8 |
| 34.884 | 2.3 |
| 36.499 | 4.8 |
| 37.427 | 2.9. |

Figure 4:
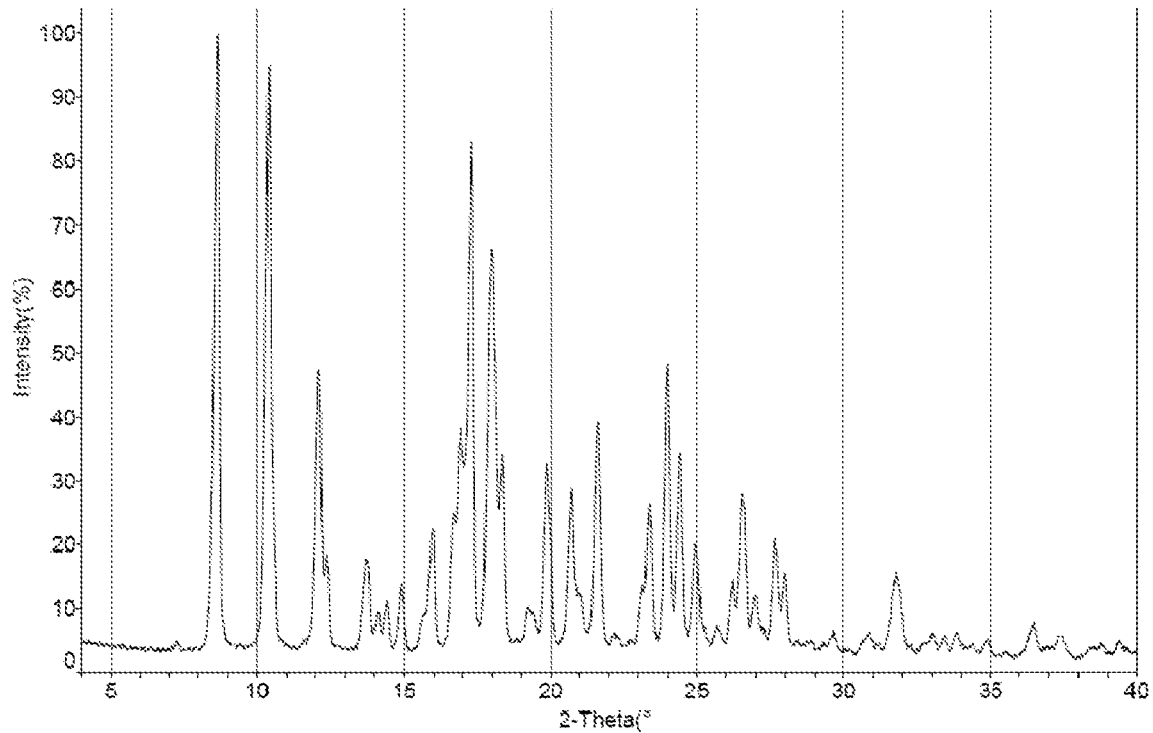
FIG. 4 is a XRPD pattern of Cu—K alpha radiation for crystal form IV of compound 5-3.

2. The crystal form of compound 5-3 of claim 1, wherein the crystal form is crystal form IV whose XRPD pattern is shown in FIG. 4.

3. A process for preparing the crystal form of compound 5-3 of claim 1, comprising:

adding crystal form I of compound 5-3 into a second organic solvent, dissolving at room temperature or heating to a temperature of 40° C. to reflux temperature for dissolution, then slowly adding a third organic solvent dropwise, and after the addition is completed, forming the crystal form IV at room temperature or by cooling to 20-30° C. in 1-120 hours;

the second organic solvent is selected from methanol, ethanol, isopropanol, n-butanol, ethyl formate, ethyl acetate, isopropyl acetate, isobutyl acetate, n-butyl acetate, acetonitrile, dichloromethane and a mixture thereof;

the third organic solvent is water;

and the XRPD pattern analysis of crystal form I of compound 5-3 is as follows:

| diffraction angle 2θ | relative intensity (%) |
|---|---|
| 8.611 | 100.0 |
| 10.330 | 70.6 |
| 12.284 | 13.4 |
| 13.703 | 23.9 |
| 14.057 | 5.6 |
| 14.351 | 4.8 |
| 14.848 | 9.2 |
| 15.576 | 7.5 |
| 16.602 | 31.6 |
| 17.250 | 71.3 |
| 17.902 | 90.7 |
| 18.277 | 42.4 |
| 19.149 | 6.5 |
| 20.625 | 21.7 |
| 21.550 | 42.7 |
| 22.124 | 2.3 |
| 23.307 | 33.4 |
| 23.953 | 2.6 |
| 24.370 | 32.3 |
| 26.501 | 29.4 |
| 26.915 | 8.7 |
| 27.663 | 11.0 |
| 27.939 | 15.5 |
| 29.499 | 2.6 |
| 30.604 | 2.2 |
| 31.727 | 13.3 |
| 32.969 | 2.6 |
| 33.378 | 2.8 |
| 33.777 | 3.0 |
| 34.825 | 1.6 |
| 36.399 | 5.3 |
| 37.366 | 4.3 |
| 39.357 | 3.3. |

4. The process according to claim 3, wherein the crystal form I is prepared by: adding compound 5-3 into ethyl acetate and pulping to provide the crystal form I.

5. The process of claim 4, wherein the compound 5-3 is prepared by the following step:

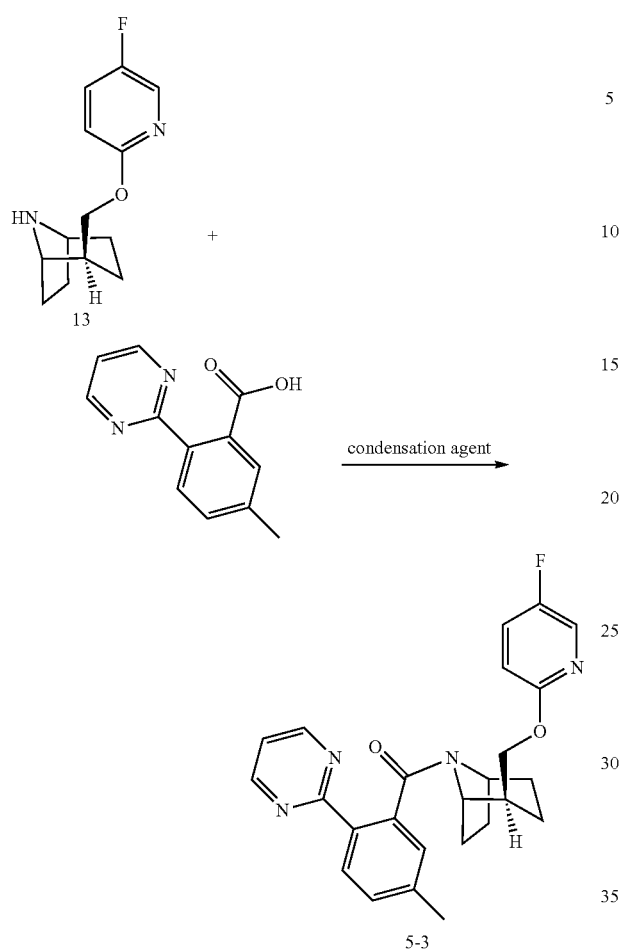

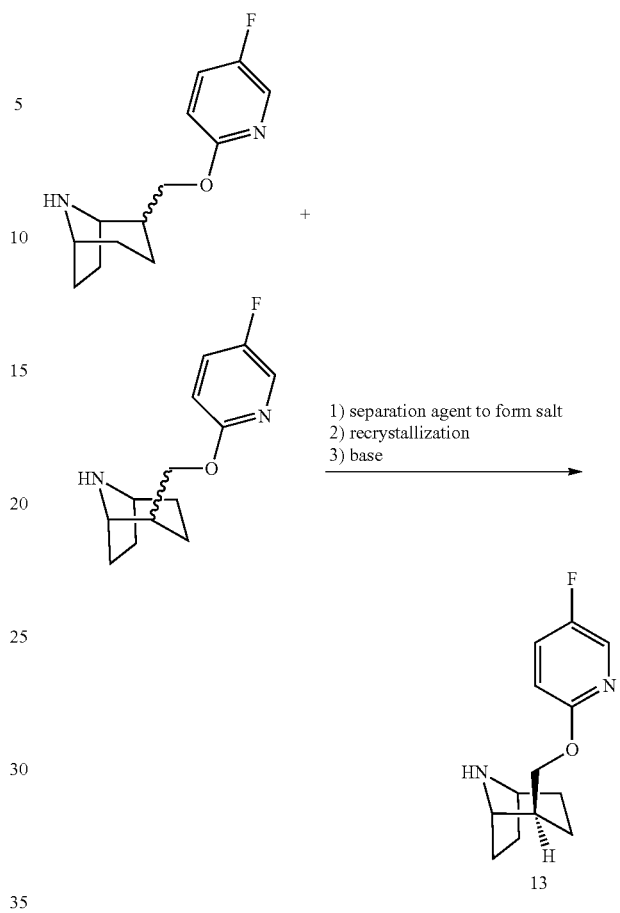

wherein the condensation agent is selected from propyl phosphoric anhydride, carbonyldiimidazole, 1-ethyl-3-(3-dimethylaminopropyl)carbodiimide, 1-hydroxybenzotriazole, or 2-(7-azobenzotriazole)-N,N,N',N'-tetramethyluronium hexafluorophosphate.

6. The process of claim 5, wherein the process for preparing compound 13 as shown in formula 13 comprises the following step:

wherein,
the separation agent is D-tartaric acid;
the reaction solvent is selected from the group consisting of ethyl acetate, isopropyl acetate, ethanol, methanol, tetrahydrofuran, dichloromethane, and water;
the recrystallization solvent is selected from the group consisting of water and ethanol; and
the base is selected from the group consisting of sodium carbonate, potassium carbonate, sodium hydroxide, and potassium hydroxide.

* * * * *